US008192946B2

(12) United States Patent
Green et al.

(10) Patent No.: US 8,192,946 B2
(45) Date of Patent: Jun. 5, 2012

(54) ASSAYS FOR DETECTING PREGNANCY-ASSOCIATED GLYCOPROTEINS

(75) Inventors: Jonathan Green, Columbia, MO (US); Bhanu Prakash Telugu, Columbia, MO (US)

(73) Assignee: The Curators of The University of Missouri, Columbia, MO (US)

( * ) Notice: Subject to any disclaimer, the term of this patent is extended or adjusted under 35 U.S.C. 154(b) by 414 days.

(21) Appl. No.: 12/422,231

(22) Filed: Apr. 10, 2009

(65) Prior Publication Data

US 2009/0258375 A1    Oct. 15, 2009

Related U.S. Application Data

(60) Provisional application No. 61/043,855, filed on Apr. 10, 2008.

(51) Int. Cl.
*C12Q 1/37* (2006.01)
(52) U.S. Cl. ............................. 435/23; 435/335; 435/510
(58) Field of Classification Search .................... 435/23, 435/338; 530/395; 436/510
See application file for complete search history.

(56) References Cited

U.S. PATENT DOCUMENTS

| | | | |
|---|---|---|---|
| 4,208,479 A | 6/1980 | Zuk et al. ........................ 435/7.9 |
| 4,271,140 A | 6/1981 | Bunting ........................ 436/500 |
| 4,755,460 A | 7/1988 | Bostwick et al. ............ 435/7.92 |
| 4,895,804 A | 1/1990 | Bostwick et al. ........ 435/240.27 |
| 6,322,816 B1 | 11/2001 | Zeidler et al. .................. 424/486 |
| 6,787,324 B2 | 9/2004 | Jordan et al. ................... 436/518 |
| 6,869,770 B1 | 3/2005 | Roberts et al. .................. 435/7.1 |
| 7,393,696 B2 | 7/2008 | Roth et al. ..................... 436/510 |
| 7,575,861 B2* | 8/2009 | Lucy et al. .......................... 435/5 |
| 7,604,950 B2* | 10/2009 | Mathialagan et al. ......... 435/7.1 |
| 7,763,432 B2* | 7/2010 | Roberts et al. .................. 435/7.1 |
| 2005/0100975 A1 | 5/2005 | Roberts et al. ............... 435/7.92 |
| 2006/0199235 A1 | 9/2006 | Lucy et al. ...................... 435/7.1 |
| 2007/0166773 A1 | 7/2007 | Roberts et al. ............. 530/387.1 |
| 2007/0184558 A1 | 8/2007 | Roth et al. ..................... 436/510 |
| 2010/0331206 A1* | 12/2010 | Roberts et al. ..................... 506/9 |
| 2011/0076705 A1* | 3/2011 | Mathialagan et al. ....... 435/7.94 |

FOREIGN PATENT DOCUMENTS

| WO | WO 99/47934 | 9/1999 |
|---|---|---|
| WO | WO 2009/076632 | 6/2009 |
| WO | WO 2006/073447 | 7/2009 |

OTHER PUBLICATIONS

Guruprasad K. et al. Comparative Modeling and Analysis of Amino Acid Substitutions . . . Protein Engineering 9(10)849-856, 1996.*
Atkinson et al., "Characterization of placentation-specific binucleate cell glycoproteins processing a novel carbohydrate," *J. Biol. Chem.*, 268(35):26679-26685, 1993.
Green et al., "Pregnancy-associated bovine and ovine glycoproteins exhibit spatially and temporally distinct expression patterns during pregnancy," *Biol. of Repro.*, 62:1624-1631, 2000.

Green et al., "Pregnancy-associated glycoproteins of the horse," *Biol Reprod*, 50 (Suppl 1):152, 1994.
Green et al., "Pregnancy-associated glycoproteins: A family of catalytically inactive aspartic proteinases," *Mol Biol Cell*, 6 (Suppl 1):454, 1995.
Green et al., "The establishment of an ELISA for the detection of pregnancy-associated glycoproteins (PAGs) in the serum of pregnant cows and heifers," *Theriogenology*, 63:1481-1503, 2005.
Guillomot, "Cellular interactions during implantation in domestic ruminants," *J. Reprod. Fertil.*, 49(Supp.):39-51, 1995.
Guruprasad et al., "Comparative modeling and analysis of amino acid substitutions suggests that the family of pregnancy-associated glycoproteins includes both active and inactive aspartic proteinases," *Protein Engin.*, 9:849-856, 1996.
Haig, "Genetic conflicts in human pregnancy," *Rev. Biol.*, 68:495-532, 1993.
Hughes et al., "Adaptive diversification within a large family of recently duplicated, placentally expressed genes," *Proc. Natl. Acad Sci., USA*, 97:3319-3323, 2000.
Humblot et al., "Diagnosis of pregnancy by radioimmunoassay of a pregnancy-specific protein in the plasma of dairy cows," *Theriogenology*, 30(2):257-267, 1988.
Humblot et al., "Pregnancy-specific protein B, progesterone concentrations and embryonic mortality during early pregnancy in dairy cows," *J. Reprod. Fert.*, 83:215-223, 1988.
Humblot, "Protéines spécifiques de la gestation chez les ruminants," *Reprod. Nutr. Dévelop.*, 28(6B):1753-1762, 1988. (French).
Humblot, "Proteins specific for gestation in ruminants," *Reprod. Nutr. Dévelop.*, 28(6B):1753-1762, 1988. (English).
Inoue et al., *Aspergillus niger* var. Macrospores proteinase B. cDNA cloning, expression, and activation of the proteinases, *Aspartic Proteinases*, 581-587, 1995.
Ishiwata et al., "Characterization of gene expression profiles in early bovine pregnancy using a custom cDNA microarray," *Mol Reprod Dev.*, 65(1):9-18, 2003.
Karen et al., "Early pregnancy diagnosis in sheep by progesterone and pregnancy-associated glycoprotein tests," *Theriogenology*, 59:1941-1948, 2003.
King et al., "Development of the bovine placentome from days 20 to 29 of gestation," *J. Reprod. Gertil.*, 59:95-100, 1980.
Kiracofe et al., "Pregnancy-specific protein B in serum of postpartum beef cows," *J. Anim. Sci.*, 71:2199-2205, 1993.
Mialon et al., "Detection of pregnancy by radioimmunoassay of a pregnancy serum protein (PSP60) in cattle," *Reprod. Nutr. Dev.*, 34:65-72, 1994.
Mialon et al., "Peripheral concentrations of a 60-kDa pregnancy serum protein during gestation and after calving and in relationship to embryonic mortality in cattle," *Reprod. Nutr. Dev.*, 33:269-282, 1993.
Patel et al., "Effect of fetal mass, number, and stage of gestation on pregnancy-specific protein B concentrations in the bovine," *Theriogenol.*, 44:827-833, 1995.
Patel et al., "Plasma bovine pregnancy-associated glycoprotein concentrations throughout gestation in relationship to fetal number in the cow," *Eur. J. Endoc.*, 137:423-428, 1997.

(Continued)

*Primary Examiner* — Ralph Gitomer
(74) *Attorney, Agent, or Firm* — SNR Denton US LLP

(57) ABSTRACT

Disclosed are methods and compositions for detecting pregnancy in an animal by means of assaying peptidase activity of one or more Pregnancy Associated Glycoproteins (PAGs). In certain aspects, methods also comprising use of an antibody that binds immunologically to a PAG that displays proteolytic activity are provided. Substrates of proteolytic PAGs are also provided, as are kits, and methods of use. Further, methods of purifying PAGs based on their proteolytic activity are also provided.

24 Claims, 9 Drawing Sheets

OTHER PUBLICATIONS

Ranilla et al., "Plasmatic profiles of pregnancy associated glycoprotein and progesterone levels during gestation in churra and merino sheep," *Theriology*, 42(3):537-545, 1994.

Roberts et al., "Glycoproteins of the aspartyl proteinase gene family secreted by the developing placenta," *Aspartic Prot., Struct, Funct., Biol., Biom Impl.*, 231-240, 1995.

Roberts et al., "Maternal Recognition of pregnancy," *Biol. Reprod.*, 54:294-302, 1996.

Sasser et al., "Characterizations of pregnancy-specific protein B in cattle," *J. Reprod. Fertil.*, 37(suppl.):109-113, 1989.

Sasser et al., "Detection of pregnancy by radioimmunoassay of a novel pregnancy-specific protein in serum of cows and a profile of serum concentrations during gestation," *Biol. Reprod.*, 35(4):936-942, 1986.

Scott et al., "Serum levels of pregnancy-associated alpha2-glycoprotein during pregnancy in autoimmune thyroid disease: relationship to disease activity," *Clinical and Experimental Immunology*, 59:564-570, 1985.

Stanley et al., "Use of a new and rapid milk progesterone assay to monitor reproductive activity in the cow," *Veterinary Record*, 664-667, 1986.

Stefanakis et al., "Development of a simple and reliable immunoenzymatic technique for the estimation of progesterone concentration in cows milk and sows serum," *Bull. Hellenic Vet. Med. Soc.*, 45:37-43, 1994. (Russian).

Stefanakis et al., "Development of a simple and reliable immunoenzymatic technique for the estimation of progesterone concentration in cows milk and sows serum," *Bull. Hellenic Vet. Med. Soc.*, 45:37-43, 1994. (English).

Szafranska et al., "Gene for porcine and bovine pregnancy-associated glycoprotein 2: Its structural organization and analysis of its promoter," *Mol. Reprod. Dev*, 66:137-146, 2001.

Szafranska et al., Porcine pregnancy-associated glycoproteins: new members of the aspartic proteinase gene family expressed in trophectoderm, *Biol. Reprod.*, 53:21-28, 1995.

Szenci et al., "Evaluation of false ultrasonographic diagnoses in cows by measuring plasma levels of bovine pregnancy-associated glycoprotein 1," *Vet. Record*, 142(12):304-306, 1998.

Takahashi et al., "Simple purification procedure for bovine pregnancy-associated glycoprotein with pepstatin A-coupled affinity chromatography," *Journal of Reproduction and Fertility, Abstract Series*, 26:32, 2000. Abstract.

Telugu et al., "Characterization of the peptidase activity of recombinant porcine pregnancy-associated glycoprotein-2," *J. Biochem.*, 144(6):725-732, 2008.

Wedemayer, "Structural insights into the evolution of an antibody combining site," *Science*, 276(5319):1665-1669, 1997.

Wooding et al., "Light and electron microscope immunocytochemical studies of the distribution of pregnancy associated glycoproteins (PAGs) throughout pregnancy in the cow: possible functional implications," *Placenta*, 26:807-827, 2005.

Wooding, "Current topic: the syneptitheliochorial placenta of ruminants: binucleate cell fusions and hormone production," *Placenta*, 13:101-113, 1992.

Xie et al., "A novel glycoprotein of the aspartic proteinase gene family expressed in bovine placental trophectoderm," *Biol. Reprod.*, 51:1145-1153, 1994.

Xie et al., "Identification of the major pregnancy-specific antigens of cattle and sheep as inactive members of the aspartic proteinase family," *Proc. Natl. Acad. Sci., USA*, 88:10247-10251, 1991.

Xie et al., "Multiple pregnancy-associated glycoproteins are secreted by day 100 ovine placental tissue," *Biol. Reprod.*, 57:1384-1393, 1997.

Xie et al., "The diversity and evolutionary relationships of the pregnancy-associated glycoproteins, an aspartic proteinase subfamily consisting of many trophoblast-expressed genes," *Proc. Natl. Acad. Sci., USA*, 94:12809-12816, 1997.

Xie et al., The gene encoding bovine pregnancy-associated glycoprotein-1, an inactive member of the aspartic proteinase family,: *Gene*, 159:193-197, 1995.

Xie et al., "Trophoblast-specific processing ans phosphorylation of pregnancy-associated glycoprotein-1 in day 15 to 25 sheep placenta," *Biol. Reprod.*, 54:122-129, 1996.

Zoli et al., "Light and electron microscopic immunolocalization of bovine pregnancy-associated glycoprotein in the bovine placentome," *Biol. Reprod.*, 46:623-629, 1992.

Zoli et al., "Purification and characterization of a bovine pregnancy-associated glycoprotein," *Biol. Reprod.*, 45:1-10, 1991.

Zoli et al., "Radioimmunoassay of a bovine pregnancy-associated glycoprotein in serum: its application for pregnancy diagnosis," *Biol. Reprod.*, 46:83-92, 1992.

Telugu et al., "An examination of the proteolytic activity for bovine pregnancy-associated glycoproteins 2 and 12," *Biol Chem.*, 391(2-3):259-270, 2010.

Chen et al., "An Aspartic Proteinase Expressed in the Yolk Sac and Neonatal Stomach of the Mouse," *Biology of Reproduction*, 65:1092-1101, 2001.

Hughes et al., "Aspartic Proteinase Phylogeny and the Origin of Pregnancy-Associated Glycoproteins," *Mol. Biol. Evol.*, 20(11):1940-1945, 2003.

Avalle et al., "Development of monoclonal and polyclonal antibodies against bovine pregnancy-associated glycoproteins (PAG) for use as reagents in localization of PAG expression and for pregnancy detection," *Biology of Reproduction, Society for the Study of Reproduction*, 64(suppl. 1)341, 2001. Abstract.

Ayad et al., "Correlation of five radioimmunoassay systems for measurement of bovine plasma pregnancy-associated glycoprotein concentrations at early pregnancy period," *Res. Vet. Sci.*, doi:10.1016/j.rvsc.2008.10.003, 2008.

Birch et al., "Homology cloning of aspartic proteases from an endocrine cell line using the polymerase chain reaction," *Biochem. Biophys. Res. Commun.*, 177(3):920-926, 1993.

Cameron et al., "Evaluation of an ultrasonic Doppler probe for pregnancy diagnosis in cattle," *Austr. Vet. J.*, 70:109-111, 1993.

Campbell et al., "General properties and applications of monclonal antibodies," In: Monoclonal Antibody Technology, Campbell (Ed.), pp. 1-31, Elsevier, The Netherlands, 1986.

Davies, "The structure and function of the aspartic proteinases," *Ann. Rev. Biophys. Chem.*, 19:189-215, 1990.

Decision on Appeal regarding U.S. Appl. No. 10/655,547, dated Nov. 8, 2007.

Garabayo et al., "Caprine pregnancy-associated glycoproteins (PAG): Their cloning expression and evolutionary relationship to other PAG," *Mo. Reprod Dev*, 57:311-322, 2000.

GenPept Accession No. A61232, dated May 12, 1994.

Gerrie et al., "Pregnancy-associated alpha-2 glycoprotein: development of a sensitive enzyme-linked immunoassay and comparison of serum concentrations in adults and children," *Clinical Chimica. Acta*, 155:51-60, 1986.

Green et al., "Bovine pregnancy-associated glycoproteins (PAG) exhibit distinct expression patterns during gestation," *Biol. Reprod*, 60(Suppl 1):497, 1999.

Green et al., "Identification of a family of Kunitz domain proteins expressed in bovine and ovine trophoblast," *Biol Reprod.*, 58 (Suppl 1):310, 2003.

Green et al., "Identification of a new aspartic proteinase expressed by the outer chorionic cell layer of the equine placenta," *Biol. Reprod.*, 60:1069-1077, 1999.

\* cited by examiner

NMA: fluorescence donor
Dnp: fluorescence quencher (identification of consensus cleavage site by LC-MS)

SEQUENCE LISTING

```
<160> NUMBER OF SEQ ID NOS: 7

<210> SEQ ID NO 1
<211> LENGTH: 10
<212> TYPE: PRT
<213> ORGANISM: Artificial Sequence
<220> FEATURE:
<223> OTHER INFORMATION: Synthetic Sequence

<400> SEQUENCE: 1

Gly Lys Pro Ile Leu Phe Phe Arg Leu Lys
```

<210> SEQ ID NO 2
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(4)
<223> OTHER INFORMATION: Xaa can be any naturally occurring amino acid

<400> SEQUENCE: 2

Gly Xaa Xaa Xaa Ala Phe Pro Lys Arg Arg
1               5                   10

<210> SEQ ID NO 3
<211> LENGTH: 59
<212> TYPE: DNA
<213> ORGANISM: Artificial Sequence
<220> FEATURE:
<223> OTHER INFORMATION: Synthetic Primer

<400> SEQUENCE: 3
gactgagcgg ccgcatggat tacaaggacg atgacgataa gatagtcatt ttgcctcta       59

<210> SEQ ID NO 4
<211> LENGTH: 59
<212> TYPE: DNA
<213> ORGANISM: Artificial Sequence
<220> FEATURE:
<223> OTHER INFORMATION: Synthetic Primer

<400> SEQUENCE: 4
gtcagtcaga gtcagagtca tgactagagt ctagatgact attacactgc cggagccag       59

<210> SEQ ID NO 5
<211> LENGTH: 54
<212> TYPE: DNA
<213> ORGANISM: Artificial Sequence
<220> FEATURE:
<223> OTHER INFORMATION: Synthetic primer

<400> SEQUENCE: 5
gactctagaa tggattacaa ggacgatgac gataagatag tcattttgcc tcta            54

<210> SEQ ID NO 6
<211> LENGTH: 54
<212> TYPE: DNA
<213> ORGANISM: Artificial Sequence
<220> FEATURE:
<223> OTHER INFORMATION: Synthetic primer

<400> SEQUENCE: 6
gatctatgat ctcagtactg cggccgctca ctattacacc tgtgccaggc caat            54

<210> SEQ ID NO 7
<211> LENGTH: 8
<212> TYPE: PRT
<213> ORGANISM: Artificial Sequence
<220> FEATURE:
<223> OTHER INFORMATION: Synthetic FLAG sequence

<400> SEQUENCE: 7

Asp Tyr Lys Asp Asp Asp Asp Lys
1               5

ASSAYS FOR DETECTING PREGNANCY-ASSOCIATED GLYCOPROTEINS

This application claims the priority of U.S. Provisional Appl. Ser. No. 61/043,855, filed Apr. 10, 2008, the entire disclosure of which is incorporated herein by reference.

BACKGROUND OF THE INVENTION

I. Field of the Invention

The present invention relates generally to the field of animal sciences. More specifically, the invention relates to methods and compositions for detecting early stage pregnancy, relating to proteolytic activity.

II. Related Art

Pregnancy diagnosis is a critical aspect of sound reproductive management in the cattle (e.g. dairy and beef) industry. In general, artificial insemination is successful less than 50% of the time and the producer must either rely on overt signs of return to estrus (that are easily missed) or delay rebreeding until pregnancy failure is confirmed by ultrasound, palpation or by assay of circulating pregnancy-specific antigens. Such delays are extremely costly and constitute a major economic loss to the industry.

An accurate pregnancy test for cattle which can be performed early in pregnancy has long been sought. Several pregnancy tests are available, including a milk progesterone assay (Oltenacu et al., 1990; Markusfeld et al., 1990), estrone sulfate analysis (Holdsworth et al., 1982; Warnick et al., 1995), rectal palpation (Hatzidakis et al., 1993), and ultrasound (Beal et al., 1992; Cameron and Malmo, 1993), or by assay of pregnancy-specific antigens, among others.

Pregnancy-associated glycoproteins (PAGs) are a family of proteins structurally related to aspartic proteinases such as pepsins, and are expressed in the outer epithelial cell layer (trophoblasts) of the placenta of even-toed ungulates (Green et al., 2000; Hughes et al., 2003; Xie et al., 1997a). Ruminant PAGs have not yet been shown to be catalytically active as proteinases, although each appears to possess a cleft capable of binding peptides (Guruprasad et al., 1996). It is estimated that cattle, sheep, and most probably all ruminant Artiodactyla possess dozens of PAG genes. Other artiodactyls, such as swine, also have PAG genes. Polypeptides with somewhat related sequences are also known to exist in species outside the Artiodactyla, including horses, cats and rodents.

Many members of the ruminant PAG family are able to enter the maternal circulation during pregnancy. Due to the placenta-specific origin of these proteins, their presence in maternal blood can serve as a means of determining pregnancy status of bred cattle. Indeed, immunological-based assays have been used as the basis for making such determinations (e.g. U.S. Pat. No. 6,869,770).

Phylogenetically, the ruminant PAGs are a highly diverse family that fall in two distinct groupings: the more recently evolved 'modern' PAGs and the 'ancient' PAGs. Even in initial protein purification studies (Butler et al., 1982; Zoli et al., 1991; Xie et al., 1991; Xie et al., 1994; Xie et al., 1996), it was clear that the boPAGs were heterogeneous in molecular weight and charge, and as more isoforms were purified, it was evident that they differed in their amino terminal sequences (Atkinson et al., 1993; Xie et al., 1997a). Despite their relationship to aspartic proteinases, many PAGs, particularly those in the modern grouping, are incapable of proteolytic activity due to site-specific mutations within the catalytic site (Green et al., 1998, Telugu et al., 2005).

Several peptidases have been shown to be products of the placenta or of the uterine decidua. Some, such as pro-renin, placental leucine aminopeptidase, pregnancy-associated plasma protein A (IGF binding protein 4-peptidase) and neutral IGFBP-3 protease, are able to enter the maternal circulation (Bischof, 1989; Poisner, 1998; Irwin et al., 2000; Bischof, 2001; Nomura et al., 2005). Often, the activity of these peptidases in serum is monitored by zymography. The proteolytic activity of neutral IGFBP-3 protease (as measured by the cleavage of a specific protein substrate (IGFBPs)) has been shown to increase in maternal serum throughout the course of pregnancy (Irwin et al., 2000). Other clinical measures of enzymes circulating in the blood (some being peptidases) have been used to monitor various physiological states (Murooka et al., 2001; Clements et al., 2004; Wu et al., 2004; Deegan et al., 2005; Sidikou et al., 2005; Zitouni et al., 2005; Villanueva et al., 2006). However, there are no known reports that describe the measurement of proteolytic activity as a means for pregnancy diagnosis in ungulates. Thus there remains a need to provide additional assay platforms for accurate and early detection of pregnancy, especially in agriculturally important animals such as cattle.

SUMMARY OF THE INVENTION

One aspect of the present invention provides compositions and methods for testing for pregnancy in an Artiodactyl animal comprising: (a) obtaining a sample comprising at least one PAG with proteolytic activity from the animal; (b) contacting the sample with a substrate for proteolysis; and (c) measuring the level of proteolytic activity in the sample, wherein an elevated level of proteolytic activity relative to the level in a non-pregnant Artiodactyl animal indicates that the animal is pregnant. In one embodiment, the Artiodactyl animal is a bovine animal. In particular embodiments, the sample is obtained from the animal between days 16 to 30 post-insemination. In certain embodiments, the sample is obtained from the animal at day 20, 21, 22, 23, 24, 25, 26, 27 or 28 post-insemination. The method of claim 1, further comprising measuring the level of proteolytic activity of more than one PAG. In certain embodiments, the PAG is selected from the group consisting of boPAG-2, boPAG-6, boPAG-8, boPAG-9, boPAG-10, boPAG-12, and poPAG-2.

The PAG may be present in early pregnancy, and in certain embodiments, the sample is selected from the group consisting of serum, plasma, whole blood, milk or urine. The PAG is present throughout pregnancy. Alternatively, in some embodiments the PAG is present in early pregnancy and absent at about two months post-partum.

In some embodiments the proteolytic activity is inhibited by pepstatin A. In certain embodiments, measuring the level of proteolytic activity in the sample comprises detection of a product of proteolysis. In particular embodiments detection comprises a calorimetric, luminescent, spectrophotometric, or fluorescent method. In some embodiments the substrate for proteolysis is selected from the group consisting of a cathepsin D substrate, a cathepsin E substrate, and a peptide comprising SEQ ID NO:2. In certain embodiments, proteolytic activity is measured at a pH of about 2.5 to about 7.0. In particular embodiments, proteolytic activity is measured at a pH of between about 2.5 and about 5.5, or at about at a pH of between about 3 and about 5.

In some embodiments, the step of increasing the proportion of a PAG in the sample occurs prior to step (b) or step (c). In other embodiments increasing the proportion of a PAG in the sample comprises contacting the sample with a lectin or with an antibody. In certain embodiments, increasing the proportion of a PAG comprises contacting a PAG with a monoclonal or polyclonal antibody that specifically binds to a PAG. In particular embodiments, the polyclonal or monoclonal antibody is selected from the group consisting of 2D9, A6, L4, and J2.

In certain embodiments, at least about 1 ng of a proteolytically active boPAG is present per sample. In particular embodiments, at least about 5 ng of a proteolytically active boPAG is present per sample. In other embodiments, at least about 10 ng of a proteolytically active boPAG is present per sample.

Another aspect of the invention comprises a kit comprising: (a) a substrate for a proteolytic PAG; (b) a means to measure proteolytic activity of at least a first PAG; and (c) a container for the substrate. In certain embodiments, the kit further comprises at least one antibody that binds to a PAG, wherein the at least one antibody is attached to a support. In particular embodiments of the invention, the support is a polystyrene plate, test tube or dipstick. The kit may further comprise a substrate comprising a detectable label. In certain embodiments the detectable label is a fluorescent, radioactive, chromogenic, or chemiluminescent tag. In other embodiments, the detectable label is a product released from the enzymatic activity of at least one PAG.

Yet another aspect of the invention is a method of purifying at least a first pregnancy associated antigen (PAG), comprising: a) obtaining a sample comprising at least a first pregnancy associated antigen (PAG); and b) purifying the PAG relative to the sample based on the proteolytic activity of the PAG. In certain embodiments, the sample is obtained from day 50 to day 250 bovine placenta. In other embodiments, the sample is obtained from day 61 to 250 bovine placenta. In some embodiments, purifying comprises immunoprecipitation, radioimmunoassay, ELISA, western blot, or immunoaffinity chromatography.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A: Recombinant bovine PAG-2 (expressed as a fusion protein with the FLAG peptide) was purified by anti-FLAG affinity chromatography. Recombinant PAG-2 was expressed in a baculovirus expression system, and insect cell lysates were applied to an anti-FLAG monoclonal antibody matrix (Sigma), washed and eluted with 3M $MgCl_2$. The presence of PAG-2 in the load, flow-through (FT) and eluted fractions was detected by Western blotting with anti-PAG-2 polyclonal antibodies (middle panel) and with anti-FLAG monoclonal antibodies (right panel). FIG. 4B: Recombinant bovine PAG-12 expressed and purified by anti-FLAG affinity chromatography as for PAG-2 in FIG. 4A is shown in the left panel of FIG. 4B; a western blot (right panel of FIG. 4B) was performed on elution fractions with the anti-FLAG monoclonal antibody. FIG. 4C: western blots performed on insect cell lysates with other candidate recombinant bovine PAGs that were generated similarly to those described in FIGS. 4A and 4B. The western blot was performed with the anti-FLAG monoclonal antibody.

In FIG. 5A, triangles represent boPAG-2 activity, which is at a maximum at pH 4, while squares represent boPAG-12 activity. In both panels (A and B), each activity point is normalized by the maximum activity (relative fluorescence units) of each peptidase at its optimal pH. The percent activity is shown on the Y-axis and the pH of respective buffers on the X-axis. The error bars represent standard deviation in results obtained from duplicate reads from two separate experiments.

DETAILED DESCRIPTION OF ILLUSTRATIVE EMBODIMENTS

Figure 1:
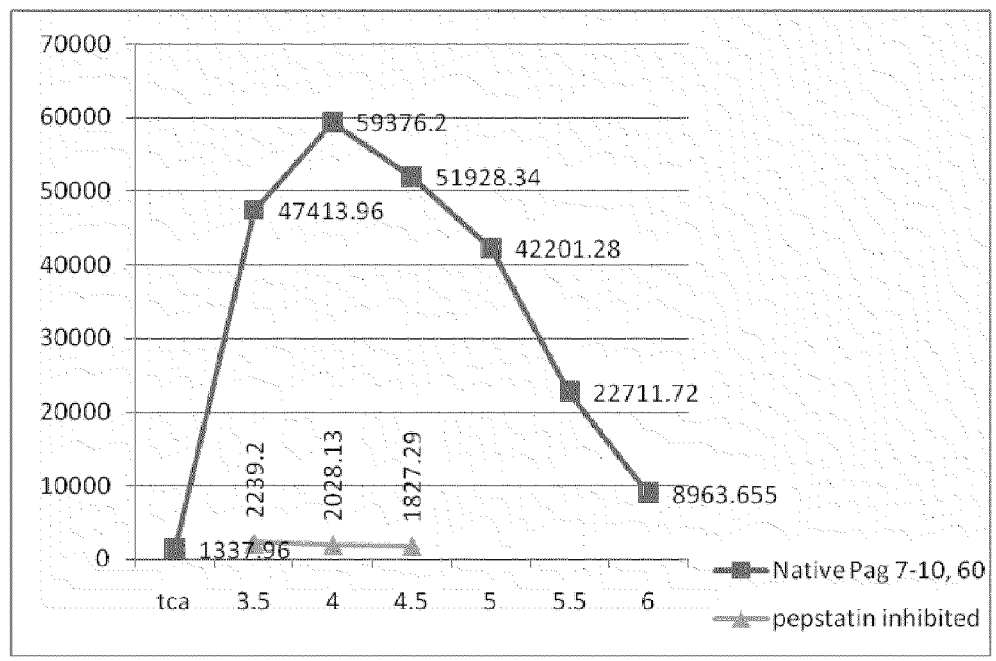
FIG. 1. pH profile of the activity of native bovine PAG (preparation 7-10) against a fluorescent peptidase substrate. The PAG was isolated by pepstatin affinity chromatography and further purified by anion exchange chromatography. Identical amounts of the 7-10 preparation were mixed with a fluorescent peptidase substrate in the presence of buffers adjusted to different pH levels. The extent of fluorescent product release is indicated on the y-axis and the pH conditions of each reaction are indicated on the x-axis. Parallel samples in the pH 3.5, 4 and 4.5 buffers were treated with pepstatin A, an inhibitor of aspartic peptidases, to determine if any observed activity was from aspartic peptidases.

Several candidate PAG polypeptides have now been confirmed as possessing proteolytic activity. This allows for development of methods for determining the pregnancy status of an animal, such as a bovine animal, by assaying for and quantifying PAG-related proteolytic activity in a sample obtained from the animal. The ability to measure proteolytic activity provides a diagnostic tool for determining the pregnancy status of the animal.

Specificity of these assays may be enhanced by linking the protease assay with an immuno-specific step, for instance by trapping or immobilizing candidate PAG polypeptides prior to assaying for proteolytic activity. The measure of PAG proteolytic activity—particularly the use of PAG-specific peptide substrates—could improve overall specificity. In addition, the use of peptidase substrates provides a different approach to pregnancy diagnosis and may help streamline the current PAG assay by decreasing the number of steps required to measure these proteins in biological samples. Thus, no "sandwich" type assay would be required if the activity of the PAG itself produced a detectable signal.

Proteolytic activity of PAGs from ruminants has not yet been reported. This activity thus serves as a novel additional means of pregnancy detection—either as a stand-alone assay (i.e. method) or as one that is combined with a PAG-specific ELISA or related immunoasssay method. The measurement of proteolytic activity arising from specific PAGs circulating in the blood of pregnant animals (and the absence of this activity in samples from non-pregnant animals) is a useful means of identifying circulating PAGs that display such activity. One aspect of the invention relates to a stand-alone peptidase assay (with a non-specific substrate, or a PAG-specific substrate) performed upon whole blood, sera, plasma or other biological samples (e.g. urine, milk, saliva). Evidence of a PAG-derived proteolytic activity would confirm pregnancy. Another aspect entails the use of PAG-specific antibodies as a way to immobilize and/or enrich for PAGs, prior to carrying out the protease assay. A variation on this approach makes use of lectins to immobilize PAGs, since they are glycosylated and are known to be bound by certain lectins (e.g. Klisch & Leiser, 2003). The peptide substrate can be incubated with the immobilized PAGs and evidence of proteolytic activity could be correlated with the presence or absence of PAGs in the biological sample and, therefore, the pregnancy status of the animal.

The use of novel PAG-specific peptide substrates, alone or in combination with PAG-specific antibodies, thus provides another approach to monitor the presence of circulating PAGs. In certain embodiments, the PAG-specific peptide substrate may comprise SEQ ID NO:2. For instance, a polypeptide sequence of SEQ ID NO:2 or comprised within SEQ ID NO:2 may be used a substrate for a proteolytically-based PAG assay, with the polypeptide modified such that cleavage of the polypeptide could be detected visually as a color change or by using a spectrometer, or such that cleavage produced a change in fluorescence that could be measured with a spectrofluorometer or fluorescent plate reader. The use of specific peptide substrates may be exploited for streamlining the detection assay. Both RIAs and ELISAs are relatively complicated multi-step assays that can make them labor- and time-intensive. The measurement of proteolytic activity from the PAGs (e.g. by luminescence (for instance fluorescence or chemiluminescence), color detection, radiography, or zymography) could simplify and considerably shorten the time needed for the assay by decreasing the overall time from start to finish and by decreasing the number of steps required.

The test may be performed early, such as 21-30 days following insemination as this is the time in which the early placenta is making intimate contacts with the maternal system and when placental products like the PAGs begin to appear in the maternal circulation. The test may be used in any of a variety of formats, such as with test tubes or ELISA plates. In particular embodiments, the test utilizes a calorimetric or fluorescent assay to detect peptidase activity. In other embodiments, a chemiluminescent, radiographic, zymographic, or other assay may be used to detect proteolytic activity. Embodiments of the present methods can be performed easily prior to 30 days following artificial insemination, and are highly sensitive and specific.

The invention also relates to a PAG-specific peptide substrate. Thus, peptide substrates specific for one or more PAG-associated proteolytic activity(-ies) are provided, which can be applied in methods to detect pregnancy in a subject. In particular embodiments, the PAG-specific proteolysis substrates may comprise SEQ ID NO:2 including ones identified from the library shown in FIG. 7. A substrate may be specific for one or more PAGs as opposed to any other proteolytic activity present in a sample. Alternatively, a substrate may be specific for one or more PAGs, such as boPAG-2 or boPAG-12, and allow one of skill to distinguish between different PAGs within a sample, for instance independent of, or in conjunction with, an immuno-assay.

A kit comprising reagents for detection of PAGs with proteolytic activity is also contemplated as an object of this invention. The kit may include a substrate or substrates for a PAG peptidase, and in certain embodiments may also comprise reagents for immunological detection of a PAG.

All the essential materials and/or reagents required for detecting PAGs that display peptidase activity in a sample may be assembled together in such a kit. This generally will comprise a peptidase substrate of interest in the practice of the present invention. Also included may be enzymes or other reagents suitable for detecting proteolytic activity and for detecting a PAG by an immune-based method, and, for instance, buffers to provide the necessary reaction conditions. Such kits generally will comprise, in suitable means, distinct containers for any reagent or enzyme, or for performing a given step in the contemplated proteolysis assay.

I. Peptides and Polypeptides

Figure 7:
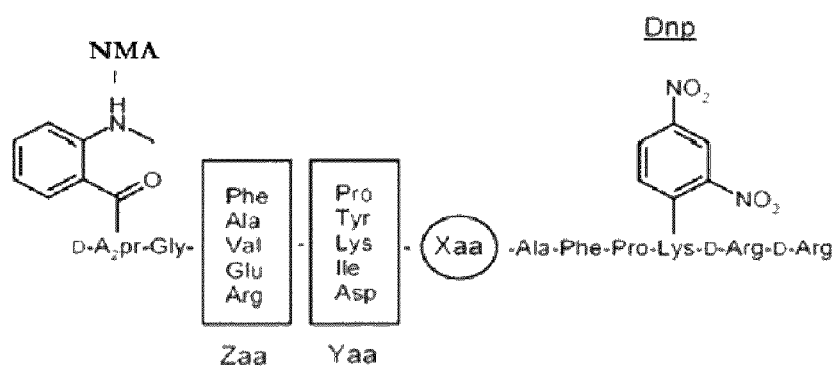
FIG. 7. A diagram representing the synthetic fluorescent substrate library used to identify PAG-specific preferences in amino acid binding within the substrate binding pockets of the active sites. There are 19 peptides that are distinguished by the particular amino acid present in the Xaa position. Positions Yaa and Zaa are occupied by one of the five amino acids specified in the figure.

Some embodiments of the invention set forth herein pertain to isolated and purified peptides and polypeptides that include a PAG peptidase substrate, one example of which comprises SEQ ID NO: 1. A "polypeptide" as used herein refers to a consecutive amino acid segment of any length. In some embodiments of the present methods, the polypeptides employed therein comprise a sequence of consecutive amino acid residues that includes within its sequence an amino acid sequence having $\geq$90% or 95% sequence identity to SEQ ID NO:1 or SEQ ID NO:2, and which serves as a substrate for PAG-mediated proteolytic activity. A "peptide" refers to a compound containing two or more amino acids in which the carboxyl group of one amino acid is linked to the amino group of another amino acid. In a particular embodiment, the peptide or polypeptide which is a substrate of a proteolytic PAG comprises SEQ ID NO:2, and Xaa as shown in FIG. 7 is selected from the group consisting of Ala, Gln, Ile, Leu, Phe, Thr, and Tyr if the proteolytic PAG being detected is boPAG-2; or is selected from the group consisting of Ala, Asp, Asn, Glu, His, Ile, Leu, Lys, Met, Phe, Pro, Thr, Tyr, and Val, if the proteolytic PAG being detected is boPAG-12. One of ordinary skill in the art would understand how to generate such a (poly)peptide which is a substrate of a proteolytic PAG in view of the disclosure set forth herein and using any of a number of experimental methods well-known to those of skill in the art. Thus, for instance, substitutions may be made that do not abolish the ability of a proteolytic PAG to bind to or cleave the peptide or polypeptide substrate.

The term "percent sequence identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (1988); Biocomputing: Informatics and Genome Projects (1993); Computer Analysis of Sequence Data, Part I (1994); Sequence Analysis in Molecular Biology (1987); and Sequence Analysis Primer (1991). Preferred methods to determine identity are designed to give the best match between the sequences tested. Methods to determine identity and similarity are codified in publicly available computer programs. Sequence alignments and percent identity calculations may be performed using, for instance, the Megalign program of the LASERGENE bioinformatics computing suite (DNASTAR Inc., Madison, Wis.), or the like. Multiple alignment of the sequences may be performed as is known in the art, for instance by using the Clustal method of alignment (Higgins and Sharp (1989) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

It is well understood by the skilled artisan that, inherent in the definition of a "polypeptide," is the concept that there is a limit to the number of changes that may be made within a defined portion of the molecule and still result in a molecule with an acceptable level of sequence identity or function, e.g., ability to function as a PAG, or as a substrate of a PAG.

An amino acid sequence of any length is contemplated within the definition of polypeptide as set forth herein, so long as the polypeptide retains the recited sequence identity. A plurality of distinct PAG substrate polypeptides with different substitutions may easily be made and used in accordance with the invention. Peptidomimetics and peptide analogs that bind to a proteolytic PAG are also contemplated, including ones that serve as proteolysis substrates. Further, the skilled artisan would know how to design non-peptide structures in three dimensional terms that mimic the peptides that bind to a target molecule.

The present invention may utilize PAG polypeptides purified from a natural source or from recombinantly-produced material. Those of ordinary skill in the art would know how to produce these polypeptides from recombinantly-produced material. This material may use the 20 common amino acids in naturally synthesized proteins, or one or more modified or unusual amino acids. Generally, "purified" will refer to a polypeptide composition that has been subjected to fractionation to remove various other proteins, polypeptides, or peptides, and which composition substantially retains its activity. Purification may be substantial, in which the polypeptide is the predominant species, or to homogeneity, which purification level would permit accurate degradative sequencing.

Amino acid sequence variants are encompassed by the present invention, and are included within the definition of "polypeptide." Amino acid sequence variants of the polypeptide can be substitutional mutants or insertional mutants. Insertional mutants typically involve the addition of material at a non-terminal point in the peptide. This may include the insertion of a few residues; an immunoreactive epitope; or simply a single residue. The added material may be modified, such as by methylation, acetylation, and the like. Alternatively, additional residues may be added to the N-terminal or C-terminal ends of the peptide. Substituted moieties may permit the detection of cleaved peptides by chromogenic, absorbance or fluorescent detection methods.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated by reference herein). It is known that certain amino acids may be substituted for other amino acids having a similar hydropathic index or score and still retain a similar biological activity. In making changes based upon the hydropathic index, the substitution of amino acids whose hydropathic indices are within +2 is preferred, those which are within +1 are particularly preferred, and those within +0.5 are even more particularly preferred.

It is understood that an amino acid can be substituted for another having a similar hydrophilicity value and still obtain a biologically equivalent protein. As detailed in U.S. Pat. No. 4,554,101, the following hydrophilicity values have been assigned to amino acid residues: arginine (+3.0); lysine (+3.0); aspartate (+3.0+1); glutamate (+3.0+1); serine (+0.3); asparagine (+0.2); glutamine (+0.2); glycine (0); threonine (−0.4); proline (−0.5+1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within +2 is preferred, those which are within +1 are particularly preferred, and those within +0.5 are even more particularly preferred.

Changes may also be made based on known substrate specificities for proteases, including aspartic proteases such as pepsin. Combinatorial peptide or polypeptide libraries may also be screened to identify substrates of proteolytic PAGs, and to assess the relative activity of a PAG on such a substrate (e.g. as per Beyer et al., 2005).

II. Antibodies and Antibody Fragments

Particular embodiments of the present invention involve antibodies or antibody fragments. The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with the present invention. Minibodies are sFv polypeptide chains which include oligomerization domains at their C-termini, separated from the sFv by a hinge region. Pack et al. (1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

Antibody-like binding peptidomimetics are also contemplated in the present invention. Liu et al., 2003, describe "antibody like binding peptidomimetics" (ABiPs), which are peptides that act as pared-down antibodies and have certain advantages of longer serum half-life as well as less cumbersome synthesis methods.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more complementary determining regions (CDRs) from a non-human (usually a mouse or rat) immunoglobulin. The non-human immunoglobulin providing the CDRs is called the "donor" and the human immunoglobulin providing the framework is called the "acceptor". A "humanized antibody" is an antibody comprising a humanized light chain and a humanized heavy chain immunoglobulin.

The term "antibody" includes polyclonal antibodies, monoclonal antibodies (mAbs), chimeric antibodies, anti-idiotypic (anti-Id) antibodies to antibodies that can be labeled in soluble or bound form, as well as fragments, regions or derivatives thereof, provided by any known technique, such as, but not limited to, enzymatic cleavage, peptide synthesis or recombinant techniques. The antibodies set forth herein are capable of binding to a PAG.

"Polyclonal antibodies" are defined herein to refer to heterogeneous populations of antibody molecules derived from the sera of animals immunized with an antigen. These different antibodies may recognize several epitopes on the same antigen. A "monoclonal antibody" contains a substantially homogeneous population of antibodies specific to antigens, which population contains substantially similar epitope binding sites. MAbs may be obtained by methods known to those skilled in the art. See, e.g., Kohler and Milstein, 1975; U.S. Pat. No. 4,376,110; Ausubel et al., 1992); Harlow and Lane 1988; Colligan et al., 1993, the contents of which are each herein specifically incorporated by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

"Chimeric antibodies" are molecules different portions of which are derived from different animal species, such as those having variable region derived from a murine mAb and a human immunoglobulin constant region, which are primarily used to reduce immunogenicity in application and to increase yields in production. Chimeric antibodies and methods for their production are known in the art. Exemplary methods of production are described in Cabilly et al., 1984; Boulianne et al., 1984; and Neuberger et al., 1985, each of which are herein incorporated by reference in their entirety.

An "anti-idiotypic antibody" (anti-Id) is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). An exemplary method of producing such antibodies is found in U.S. Pat. No. 4,699,880, which is herein entirely incorporated by reference.

Antibodies of the present invention can include at least one heavy, at least one light chain, a heavy chain constant region, a heavy chain variable region, a light chain variable region and/or a light chain constant region, wherein a polyclonal Ab, monoclonal Ab, fragment and/or regions thereof include at least one heavy chain variable region or light chain variable region that binds a portion of a PAG.

Certain embodiments of the present invention pertain to methods for detecting pregnancy in an animal that involve obtaining a sample from the animal and detecting peptidase activity in the sample. The embodiments may further comprise contacting the sample with an antibody or antibody fragment, wherein the antibody or antibody fragment comprises a domain that binds to one or more PAG(s) that displays peptidase activity, to immobilize or at least partially isolate the PAG, and to also detect the presence of the PAG via a proteolysis assay such as a peptidase assay. That is, contacting the putatively PAG-containing sample by the antibody or antibody fragment may occur prior to, concurrently with, or subsequently to, determining the level of peptidase activity of the sample, wherein detection of the PAG(s) indicates that the animal is pregnant. Any method known to those of ordinary skill in the art can be used to identify proteolytic activity including peptidase activity, or to identify the binding of a PAG and an antibody. Examples of references which address methods for defining variable regions of IgGs include Mo et al. (1993) and Leibiger et al. (1999), herein specifically incorporated by reference. Methods for measuring proteolytic activity include, but are not limited to, zymography, spectrophotomeric methods, calorimetric methods, and fluorescence-based methods. References that address such methods include Twinging (1984), Dunn (2002), Sidikou et al. (2005), Villanueva et al. (2006), and Wu et al. (2004) (each herein incorporated by reference), among others.

III. Detection Methods and Assay Formats

Certain embodiments of the present invention pertain to methods of detecting pregnancy in an animal that involves contacting a sample obtained from an animal with a substrate of a proteolytic PAG, and detecting the cleavage of the substrate. An immunoassay may be used in conjunction with the proteolysis assay. Any method known to those of ordinary skill in the art can be used to detect proteolytic activity, as well as any antibody or antibody fragments bound to a PAG in the sample (e.g. Abriola, 1999).

The present invention therefore provides for the use of a proteolysis (e.g. peptidase) assay to detect the presence of a PAG in a ruminant animal, optionally in conjunction with the use of an antibody in detecting such a PAG. Various useful methods of detecting proteolytic activity are known, as described above. When used for diagnostic purposes, the peptides and peptide mimetics can be labeled with a detectable label and, accordingly, the peptides and peptide mimetics without such a label can serve as intermediates in the preparation of labeled peptides and peptide mimetics. Detectable labels can be molecules, or compounds, which when covalently attached to the peptides and peptide mimetics, permit detection of the peptide and peptide mimetics. Detection may occur in vivo or in vitro. Detectable labels are well known in the art and may include, for instance, radioisotopes, fluorescent labels (e.g. fluorescein), chemiluminescent labels (e.g. luciferin), other chromogenic substrate or products, and the like. The particular detectable label employed is not critical.

One or more peptidase inhibitors, such as, but not limited to, EDTA (for metalloproteinases), E64 (for cysteine proteinases), and AEBSF or related compound (for serine proteinases), among others, may also be employed to increase the sensitivity and/or specificity of the pregnancy assay. Further, various useful immunodetection methods have been described in the scientific literature, such as, e.g., Nakamura et al. (1987). Immunoassays, in their most simple and direct sense, are binding assays. Certain immunoassays are enzyme linked immunosorbent assays (ELISAs) and radioimmunoassays (RIA). Immunohistochemical detection using tissue sections also is particularly useful. However, it will be readily appreciated that detection is not limited to such techniques, and Western blotting, dot blotting, FACS analyses, and the like also may be used in connection with the present invention.

In general, immunobinding methods include obtaining a sample suspected of containing a protein, peptide or antibody, and contacting the sample with an antibody or protein or peptide in accordance with the present invention, as the case may be, under conditions effective to allow the formation of immunocomplexes. Preferred samples, according to the present invention, are fluids, such as milk, urine, blood, serum or saliva.

In particular embodiments, the antibody is linked to a solid support, such as the inner wall of a tube or well, and the sample suspected of containing the PAG will be applied to the immobilized antibody.

Antibody-coated tube systems are described in U.S. Pat. No. 3,646,346 and WO 98/16832, each of which is herein specifically incorporated by reference. Presence of PAG-antibody complexes can then be detected under specific conditions. Optionally, such immune complexes can be quantified.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any PAG present in the sample. After this time, the sample-antibody composition will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, luminescent, fluorescent, biological and enzymatic tags. U.S. Pat. Nos. concerning the use of such labels include 3,817,837; 3,850,752; 3,939,350; 3,996,345; 4,277,437; 4,275,149 and 4,366,241, each incorporated herein by reference. Methods for the immunological determination of proteins and kits for carrying out the method can be found in U.S. Pat. No. 5,721,105, herein specifically incorporated by reference.

In particular embodiments, the method involves the use of a secondary binding ligand such as a second antibody and/or a biotin/avidin ligand binding arrangement, as is known in the art. The secondary antibody employed in the detection may itself be linked to a detectable label, wherein one would then simply detect this label, thereby allowing the amount of the primary immune complexes in the composition to be determined. Methods for the detection of a biomolecule in a test sample using immunocapture, biotin/avidin amplification, and horseradish peroxidase color production can be found in U.S. Patent App. Pub. No. 2003/508381.

Usually, the primary immune complexes may be detected by means of a second binding ligand that has binding affinity for the PAG or the PAG-specific first antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the PAG or anti-PAG antibody is used to form secondary immune complexes, as described above. The second binding ligand contains an enzyme capable of processing a substrate to a detectable product and, hence, amplifying signal over time. After washing, the secondary immune complexes are contacted with substrate, permitting detection.

In one embodiment of the invention, enzyme-linked immunoassay (ELISA) may be used. See, e.g., Engvall, 1980; Engvall, 1976; Engvall, 1977; Gripenberg et al., 1978; Makler et al., 1981; Sarangadharan et al., 1984. ELISA allows for substances to be passively adsorbed to solid supports such as plastic to enable facile handling under laboratory conditions. For a comprehensive treatise on ELISA the skilled artisan is referred to "ELISA; Theory and Practise" (Crowther, 1995).

The sensitivity of ELISA methods is dependent on the turnover of the enzyme used and the ease of detection of the product of the enzyme reaction. Enhancement of the sensitivity of these assay systems can be achieved by the use of fluorescent and radioactive substrates for the enzymes. Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

In one embodiment, the invention comprises a "sandwich" ELISA, where anti-PAG antibodies are immobilized onto a selected surface, such as a well in a polystyrene microtiter plate, a tube, or a dipstick. Then, a test composition suspected of containing PAGs, e.g., a clinical sample, is contacted with the surface. After binding and washing to remove non-specifically bound immunocomplexes, the bound antigen may be detected by contacting the complex with a substrate of a proteolytic PAG in a peptidase assay, and optionally, with a second antibody to the PAG. Lectins could also be used to selectively immobilize PAGs (e.g. Klisch et al., 2006; Klisch and Leiser, 2003).

In another exemplary ELISA, polypeptides from the sample are immobilized onto a surface and then contacted with an anti-PAG antibody. After binding and washing to remove non-specifically bound immune complexes, the bound antigen-antibody complex is detected by a peptidase assay, and optionally, an immunoassay. Where the initial antibodies are linked to a detectable label, the primary immune complexes may be detected directly. Alternatively, the immune complexes may be detected using a second antibody that has binding affinity for the first antibody, with the second antibody being linked to a detectable label.

Another ELISA in which the PAGs are immobilized involves the use of antibody competition in the detection. In this ELISA, antibodies specific to PAGs are added to the wells, allowed to bind to the PAG, and detected by means of their label. The amount of PAG in a sample is determined by mixing the sample with the labeled antibodies before or during incubation with coated wells. The presence of PAG in the sample acts to reduce the amount of antibody available for binding to the well, and thus reduces the ultimate signal.

Irrespective of the format employed, ELISAs have certain features in common, such as coating, incubating or binding, washing to remove non-specifically bound species, and detecting the bound immune complexes. In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These can include bovine serum albumin (BSA), casein, solutions of milk powder or other antigenically neutral proteins. The coating allows for blocking of nonspecific adsorption sites on the immobilizing surface and thus reduces the background caused by nonspecific binding of antisera onto the surface.

"Under conditions effective to allow immune complex (antigen/antibody) formation" means that the conditions preferably include diluting the antigens and antibodies with solutions such as BSA, bovine gamma globulin (BGG), evaporated or powdered milk, and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 h to 2 h to 4 h, at temperatures preferably on the order of 25° C. to 27° C., or may be overnight at about 4° C. or so.

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid (ABTS) and $H_2O_2$, in the case of peroxidase as the enzyme label. Quantitation is then achieved by measuring the degree of color generation, e.g., using a visible spectra spectrophotometer.

IV. Purification of Proteins

Certain embodiments pertain to an isolated or purified polypeptide, or methods employing an isolated or purified polypeptide. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or polypeptide. The term "purified polypeptide, protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various techniques suitable for use in protein purification will be well known to those of skill in the art. These include, for example, precipitation with ammonium sulfate, PEG, antibodies and the like or by heat or acid pH denaturation of contaminating proteins, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the polypeptide always be provided in its most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

V. Kits

In still further embodiments, the present invention provides kits for use with the detection methods described above for the detection of PAGs, such as a peptidase detection kilt, optionally comprising an immunodetection kit, to diagnose pregnancy in a ruminant such as a bovine. In certain embodiments, a peptidase substrate comprising a domain having greater than 95-97% sequence identity to SEQ ID NO: 1 or SEQ ID NO:2 are included in the kit. The kit may include one or more containers. The container, for example, may be a vial, a tube, a flask, a vial, or a syringe.

In particular embodiments, the antibody is a monoclonal antibody or other characterized anti-PAG immunoglobulin. In one embodiment, the antibody is designated 2D9. A hybridoma cell line that produces antibody 2D9 was deposited with the Patent Depository of the American Type Culture Collection (ATCC), Manassas, Va., USA 20110-2209 on Aug. 2, 2007 and assigned Patent Deposit No. PTA-8566 (Identification Reference MON-PAG-2D9).

In further embodiments, the kit includes one or more tubes or wells of a microtiter plate with prebound antibody. Alternatively, the kit may include antibody prebound to a column matrix. The kit may allow for the assay of a single sample, or more than one sample. In some embodiments, the kit includes a plurality of microtiter plates or tubes coated with antibody which allow for immunodetection of numerous samples concurrently or consecutively.

The immunodetection reagents of the kit may take any one of a variety of forms, including those detectable labels that are associated with and/or linked to the given antibody. Detectable labels that are associated with and/or attached to a secondary binding ligand are also contemplated. Exemplary secondary ligands are those secondary antibodies that have binding affinity for the first antibody.

In some embodiments, the kits include a secondary antibody that has binding affinity for the first antibody. The second antibody may or may not be linked to a detectable label. In some further embodiments, the kit includes a third antibody that has binding affinity for the second antibody, the third antibody being linked to a detectable label. As noted above, a number of exemplary labels are known in the art and/or all such labels may be employed in connection with the present invention.

The kits may optionally include a suitably aliquoted composition of a PAG to provide for a positive control. The components of the kits may be packaged either in aqueous media and/or in lyophilized form.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Proteolytic Activity of Purified PAGs

Native Pregnancy Associated Glycoproteins (PAGs) were partially purified, initially, from bovine placenta essentially according to the method of Green et al. (2005) and Wooding et al. (2005). The native bovine PAGs were further purified via affinity chromatography and ion-exchange chromatography. Subsequent to the initial isolation, the PAG preparation was applied to a Pepstatin A-agarose affinity column at pH 7.0, and eluted in the presence of Triton® X-100 at pH 10.0.

The above affinity chromatography step was followed by application to a DEAE-anion exchange column, to remove excess Triton X-100 and other contaminating proteins (Green et al., 2005; Wooding et al., 2005). This preparation was termed "7-10".

A pH profile of peptidase (i.e. proteolytic) activity of the purified 7-10 PAG preparation using a fluorescent peptidase substrate (e.g. Peptides International Cat. No. SMO-3200-v, with fluorescent cathepsin D/E substrate MOCac-Gly-Lys-Pro-Ile-Leu-Phe-Phe-Arg-Leu-Lys(Dnp)-D-Arg-NH$_2$ (SEQ ID NO:1) is shown in FIG. 1. Units on the left axis denote fluorescence intensity at 393 nm as a result of cleavage of the substrate. Significant peptidase activity was seen with a pH optimum of 3.5-4.5. This activity could be inhibited by the aspartic peptidase inhibitor pepstatin A. 1-5 ng, or more, of active enzyme would be readily detectable, for instance in an endpoint assay, as may be quantified by titration of active sites.

Figure 2:
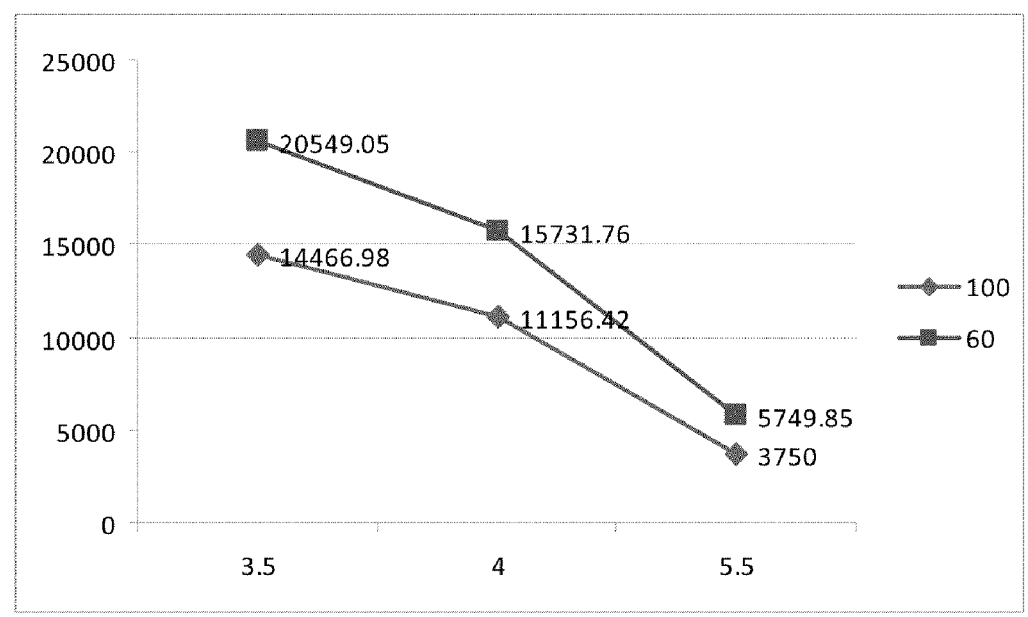
FIG. 2. pH profile of the activity of native bovine PAG (preparation 7-8) against a fluorescent peptidase substrate. Different PAGs bind and elute under distinct conditions during pepstatin affinity chromatography. Results illustrate that biochemical differences (reflected by differences in peptidase activity) exist between fractionated PAG after elution from a pepstatin affinity matrix. Identical amounts of protein were assayed and the data indicate that the 7-8, AEX 60 fraction is more active than the 100 fraction at a given pH. The "60" designation represents the fraction corresponding to a salt concentration of approximately 75 mM NaCl during elution off an anion exchange (AEX) matrix. The "100" designation represents the fraction corresponding to a salt concentration of approximately 150 mM NaCl during elution off an anion exchange (AEX) matrix.

Purification was also performed by chromatography with modified elution and/or binding pH. Thus, preparation "7-8" was obtained by binding to a pepstatin A affinity column at pH 7.0, as above, followed by elution at pH 8.0 in the presence of Triton X-100, while PAG preparation "7.5-8" was obtained by binding at pH 7.5, followed by elution at pH 8 in the presence of Triton X-100. For the 7-8 preparation, further purification was performed by DEAE anion exchange chromatography, and elution fractions 60 and 100, corresponding to 75 and 150 mM NaCl, respectively, were assayed for peptidase activity. Resulting activity is shown in FIG. 2. For preparation 7.5-8, similar DEAE anion exchange was performed as for the 7-8 preparation, and again fraction 60 (75 mM NaCl) and fraction 100 (150 mM NaCl) were assayed. Proteolytic activity is shown in FIG. 3 for the PAG 7.5-8 preparation.

Figure 3:
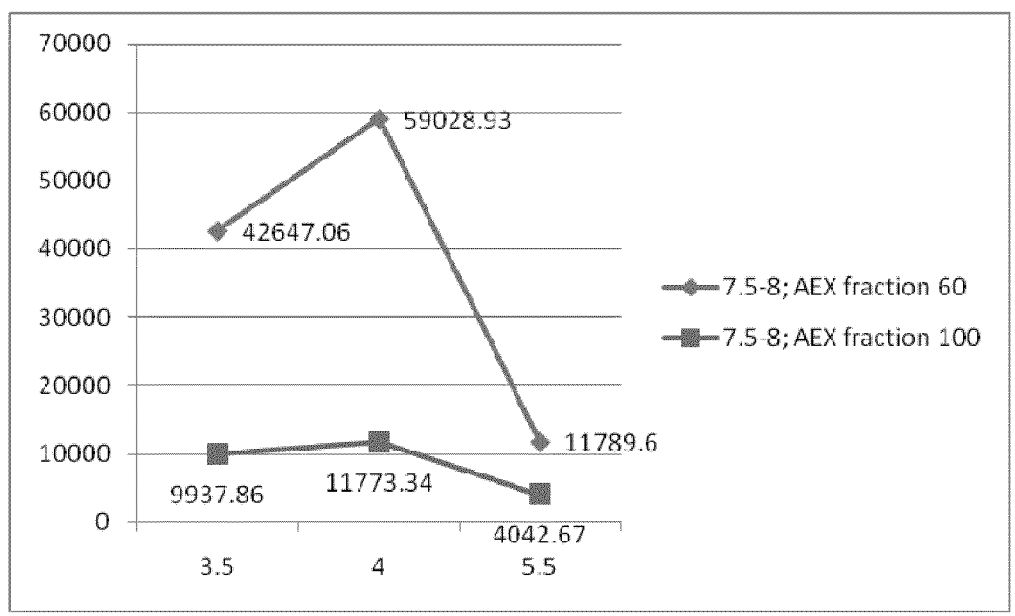
FIG. 3. pH profile of the activity of native bovine PAG preparation 7.5-8 against a fluorescent peptidase substrate. Results illustrate the biochemical differences (reflected by differences in peptidase activity) between fractionated PAG after elution from a pepstatin affinity matrix. Identical amounts of protein were assayed and the data indicate that the 7.5-8, AEX 60 fraction is substantially more active than the 100 fraction at a given pH. The "60" designation represents the fraction corresponding to a salt concentration of approximately 75 mM NaCl during elution off an anion exchange (AEX) matrix. The "100" designation represents the fraction corresponding to a salt concentration of approximately 150 mM NaCl during elution off an anion exchange (AEX) matrix.

In each of the examples shown in FIGS. 1-3, native bovine PAGs were bound to pepstatin-agarose matrix at pH 7 or 7.5, washed and eluted by increasing osmolarity (up to 1 M NaCl), including detergent (1% Triton X-100) and increasing the pH of the elution buffer. Different PAGs bind with differing affinities to the aspartic peptidase inhibitor, pepstatin A, and it is possible to isolate different members of the family by systematically altering binding and elution conditions (e.g. Green et al., 2005; Wooding et al., 2005). The differences in activity and pH optima for each of these preparations are illustrated in FIGS. 1-3. Confirmation that the activity that arose from an aspartic peptidase is found by the ability of pepstatin A to inhibit peptidase activity (FIG. 1). Activity arising from other classes of peptidases was excluded by the inclusion of class specific inhibitors in the assay buffers (1 mM EDTA (Sigma) for metalloproteinases; 10 µM E64 (Sigma) for cysteine proteinases and 4 mM AEBSF (Roche) for serine proteinases).

EXAMPLE 2

Creation of Recombinant PAGs

Recombinant bovine PAG 2 was expressed in a baculovirus expression system, as a fusion protein tagged with the FLAG® peptide (Sigma, St. Louis, Mo.).

The BD Baculogold™ Baculovirus insect cell expression system (BD biosciences Pharmingen, San Diego, Calif.) was used to express several recombinant PAGs. For example, boPAG-2 was cloned into the pvl-92 transfer vector by using the following oligonucleotides, sense: 5'-GAC TGA *GCGGCCGC*ATGGATTACAAGGACGAT GACGATAA-GATAGTCATTTTGCCTCTA-3' (SEQ ID NO:3) and antisense: 5'-GTCAGTCAGAGTCAGAGTCATGACTAGAG *TCTAGA*TGACTATTACACTGCCG GAGCCAG-3' (SEQ ID NO:4).

Bovine PAG-12 was cloned into the pacmp-3 transfer vector with the following oligonucleotides, sense: 5'-GAC *TCTAGA*ATGGATTACAAGGACGATGACGATAA GAT-AGTCATTTTGCCTCTA-3' (SEQ ID NO:5) and antisense: 5'-GATCTA TGATCTCAGTACT*GCGGCCGC*TCACTAT-TACACCTGTGCCAGGCCAAT-3' (SEQ ID NO:6). The recombinant proteins were expressed as fusion proteins with a FLAG-tag in the N-terminus of the protein. A sequence encoding for the FLAG peptide (DYKDDDDK (SEQ ID NO:7)) shown as regular bold in the sense oligonucleotide was engineered into the sequence and, thereby, incorporated into the N-terminus of the proforms of both PAG-2 and -12. Sequence encoding for restriction enzymes (bold italicized) NotI and BglII (New England Biolabs, Mass. USA) were also engineered into the sense and antisense oligonucleotides to permit directional cloning into the corresponding transfer plasmids. Once the integrity and frame of the sequences in the transfer vectors was verified by sequencing, the vectors were transfected into Sf-9 cells along with BD baculogold linearized Baculovirus DNA by using the BD baculogold transfection kit according to the manufacturer's recommendations. Following transfection, the viruses were extracted, amplified and were used to infect Sf-9 cells to generate recombinant proteins as described elsewhere (O'Reilly, 1992; Pharmingen protocol manual). Infected cells were harvested, chilled on ice, centrifuged at 600 g for 5 min at 4° C. followed by two wash cycles under similar conditions with cold 1×PBS (2.68 mM KCl, 1.47 mM $KH_2PO_4$, 136.89 mM NaCl and 8.10 mM $Na_2HPO_4$, pH 7.2). The final cell pellet was stored at −80° C. until use.

The other PAGs (recombinant boPAG-6, -8, -9, -10, -12, -17, -19, and -20, and recombinant poPAG-2) were cloned into either the pvl-92 or pvl-93 vectors, depending on what was most feasible regarding preferred restriction sites used for directional cloning into the transfer vector.

For purification of the recombinant protein, the corresponding frozen pellets were lysed on ice with I-Per insect cell protein extraction reagent (Pierce, Ill., USA). A standard cocktail of protease inhibitors, which included 0.4 mM Pefabloc SC-AEBSF (Roche Applied Science), 5 µg/mlA-protinin, 10 µM E-64, 1 mM EDTA (Sigma, Mo., USA) along with 1 mM DTT, was supplemented to the lysis buffer just before use. Following mixing and incubation with lysis buffer for at least 15 min on ice, the lysate was cleared by centrifugation at 15,093 g for 30 min and dialyzed overnight in a 30 K MWCO dialysis tubing in a buffer containing 20 mM Tris-HCl, 250 mM NaCl pH 7.4 at 4° C. All downstream purification procedures were performed in a refrigerated room at 4-6° C. The dialysed lysate was fractionated on a sephadex-200 size exclusion column (1.5 cm×106 cm) equilibrated in 20 mM Tris-HCl, pH 7.4, 150 mM salt. All fractions that were determined to have the FLAG peptide present (by dot-blot with an anti-FLAG M2 antibody) were pooled and subsequently affinity purified by using anti-FLAG M2 agarose (Sigma, Mo., USA). For affinity chromatography, the matrix was equilibrated with TBS buffer (50 mM Tris-HCl, 150 mM NaCl, pH 7.4), following which, the FLAG-containing protein samples were loaded twice onto the column by gravitational flow at approximately 0.2 ml/min. The column was then subjected to subsequent washes with 20 column volumes of wash buffer (20 mM Tris-HCl, 150 mM NaCl, pH7.4), 20 column volumes of high salt buffer (20 mM Tris-HCl, 500 mM NaCl, pH 7.4) and finally 20 column volumes of high-salt buffer supplemented with 0.1% Tween. The matrix was re-equilibrated with 10 column volumes of wash buffer, to remove residual detergent, and 10 column volumes of pre-elution buffer (10 mM phosphate buffer, pH 7.2). The column was then eluted with 5 column volumes of 50 mM phosphate buffer, 2M $MgCl_2$, pH 7.2. The protein sample was desalted by dialysis in 20 mM Tris-HCl, 250 mM salt, pH8.0 and concentrated by using an Amicon-ultra-15 with ultra cell-30 membrane (Millipore, Mass., USA). The concentrated protein samples were supplemented with the inhibitor cocktail and cold (4° C.) glycerol (to a final concentration of 10%, v/v). In most cases, the protein samples were immediately used in the assays. For long term storage, the protein sample was stored in 50% glycerol at −80° C.

Figure 4A:
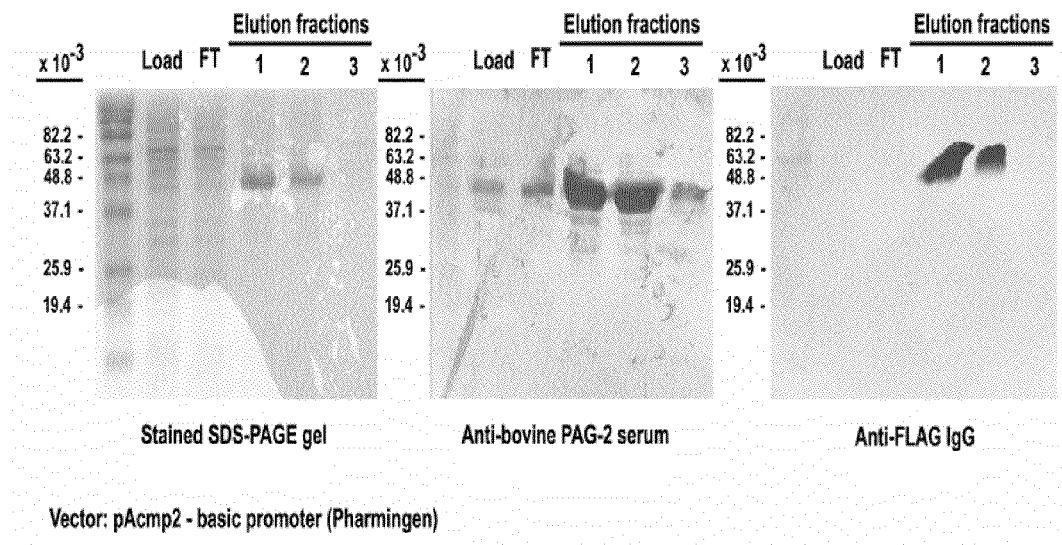
FIGS. 4A, 4B and 4C. Expression and purification of recombinant bovine PAGs.
Figure 4B:
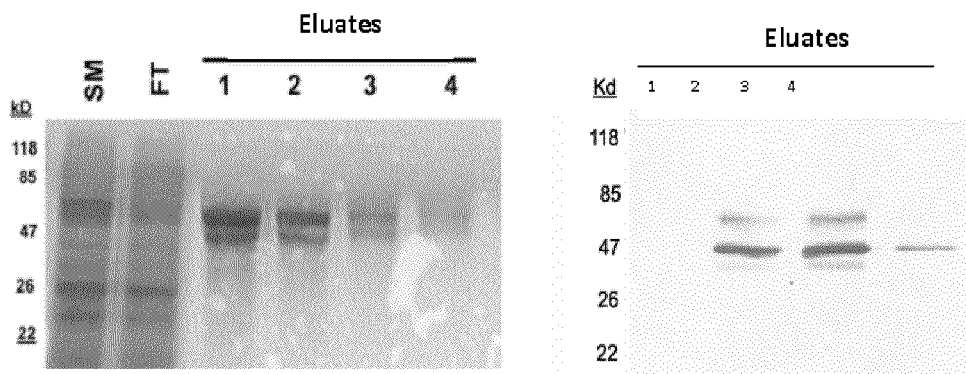
Figure 4C:
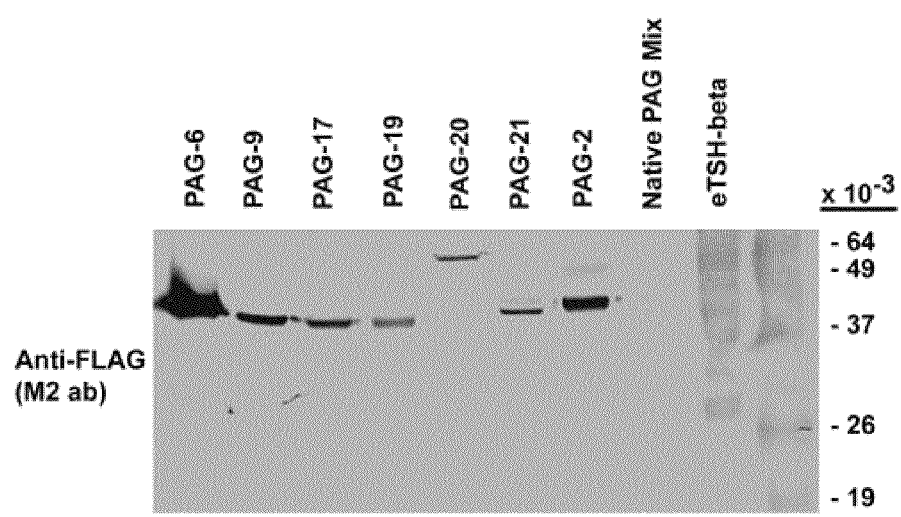

Recombinant boPAG-6, -9, -12, -17, -19, -20 and -21, and recombinant poPAG-2 were also similarly expressed and purified using an anti-FLAG® monoclonal antibody matrix (FIGS. 4B, 4C).

EXAMPLE 3

Proteolytic Activity of Recombinant PAGs

Figure 5A:
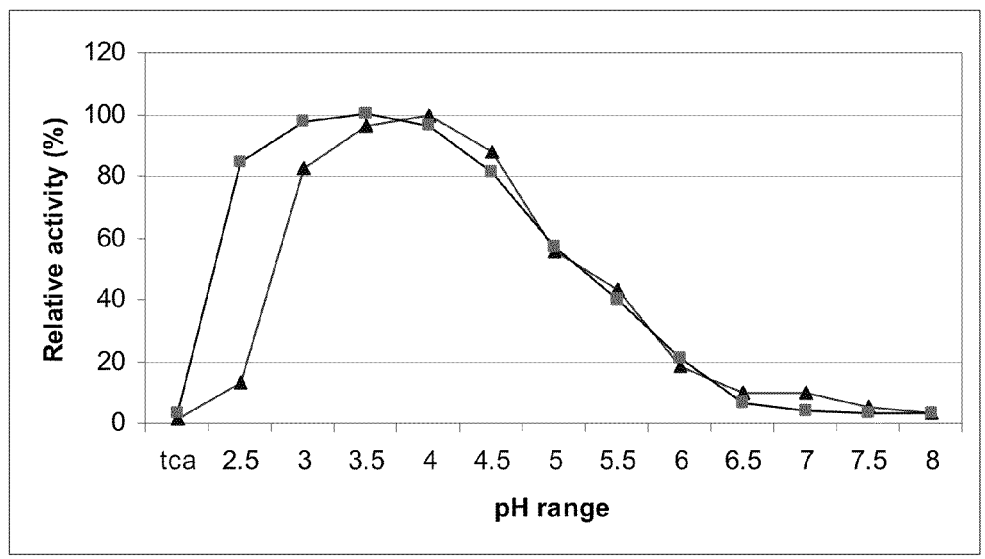
FIGS. 5A and 5B. The activity of purified recombinant bovine PAG-2 and -12 (FIG. 5A), and porcine PAG-2 (FIG. 5B), against a fluorescent cathepsin D substrate as a function of pH.
Figure 5B:
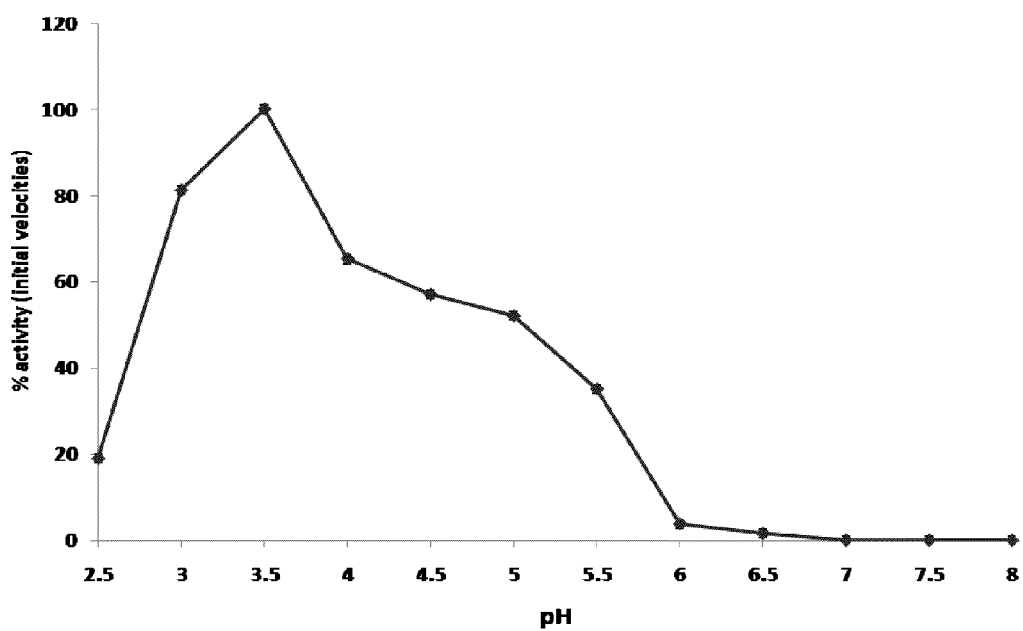

Recombinant boPAG-2 and -12 and recombinant porcine PAG-2 (poPAG-2) were tested for proteolytic activity by incubation with 20 µM fluorescent cathepsin D/E substrate (Peptides International, as above) in buffers of varying pH containing 100 mM NaCl. Raw fluorescence data was transformed to % relative activity, with the highest value set at 100%. Maximal activity for boPAG-2 was at pH 4, while maximal activity for boPAG-12 and poPAG-2 was at pH 3.5 (FIGS. 5A and 5B). Each protein displayed activity in the pH range 3-5.5. BoPAG-12 and poPAG-2 also showed activity at pH 2.5.

EXAMPLE 4

Enrichment of PAGs from Solution with Antibodies Prior to Peptidase Assay

Several antibodies were tested for their ability to selectively bind and immobilize native PAGs from solution. In each case, 1 µg of the antibodies were coated in the wells of a standard ELISA plate (coating overnight followed by storage at 4° C.). Remaining non-specific binding sites were blocked by incubation with bovine albumin for 1-2 hours. Purified PAG dilutions (a mixture of pepstatin-purified PAGs that represented 7/8, 7/10, 5/7 and 5/8 preparations) were then applied to the plate as either 5 or 50 ng of total protein in 100 µl (Table 1). After an incubation period, the plates were washed and the cathepsin D/E substrate in assay buffer was added to the wells. Several proteolytic assays are represented in Tables 1-3; each was carried out at pH 3.5, 37° C., and substrate incubation times varied from 2-8 hours depending on the experiment. Product liberation was measured on a fluorescent plate reader (Tables 1-3) at 320 nm excitation and 393 nm emission.

The antibodies employed were (a) polyclonal antibodies (POLY) raised against a mixture of native PAGs (Green et al., 2005; Wooding et al., 2005); (b) an equimolar mixture of three specific monoclonal antibodies (MONO) directed toward selected PAGs (Green et al., 2005, incorporated herein by reference); and (c) a rabbit polyclonal anti-PAG-10 (PAG-10) antibody raised against recombinant bovine PAG-10 that had been produced and purified as described above. The blank (Blank) consisted of 50 ng of bovine serum albumin and the background control (Rabbit-Ig) was rabbit immunoglobulins loaded in the same amount (1 μg per well) as the other trapping immunoglobulins. Table 1 shows the relative fluorescence (counts) of released product resulting from a representative "immuno-trap" peptidase assay with purified native bovine PAG standards. In each case, the anti-PAG antibodies were able to selectively immobilize proteolytically active PAGs from the solution as was indicated by the increase in fluorescence above that for the blank (Table 1).

TABLE 1

Fluorescent product release from immuno-trap protease assay using a purified native bovine PAG mixture.

| Trap antibody | 50 ng standard | 5 ng standard | 50 ng blank |
|---|---|---|---|
| POLY | 575724 | 573585 | 37731 |
| MONO | 103779 | 63068 | 30892 |
| PAG-10 | 75774 | 46290 | 15173 |
| Rabbit Ig (control) | | | 6037 |

Relative fluorescence was also assayed by an immuno-trap protease assay of native PAG preparations enriched to a greater extent than the PAG mixture used for the experiments in Table 1. Table 2 details the ability of polyclonal ("#20"; the same anti-PAG antibody that was used) and monoclonal antibodies to trap PAGs from solution (readings in italics are significantly different from the control). Fraction "5/7(60)" was comprised of native PAGs bound to pepstatin at pH 5.0 and eluted at pH 7.0. The PAGs in this fraction were further purified by using a DEAE-sepharose anion exchange column, and elution fraction 60 (75 mM NaCl) was used in this particular assay. PAG preparation "5/8 (60)" is a similar preparation except that a pH 8.0 buffer was used to elute the sample from the pepstatin A column. "Mixed PAG" represents pooled native PAGs from various preparations that was also used in the experiments illustrated in Table 1. An asterisk (*) in Table 2 denotes that heat-inactivated BSA was used in those assays as blocking protein and as a loading control to determine the extent, if any, that BSA might be contributing to the fluorescent signal. Row 4 of Table 2 shows results in which representative native PAGs were spiked into non-pregnant heifer serum (NPHS). The numbers in italics represent readings that are significantly different from the controls (p<0.05). In each experiment, the monoclonal and polyclonal antibodies were able to trap proteolytically active PAGs from the Mixed PAG and the 5/8 (60) preparations. The 5/7 (60) preparation was somewhat more variable; although one of the monoclonal trap experiments exhibited activity above the BSA control.

TABLE 2

Fluorescent product release from immuno-trap protease assay.

| Row # | Antibody | Protein Source | BSA | 5/7 (60) | 5/8 (60) | Mixed PAG |
|---|---|---|---|---|---|---|
| 1 | Polyclonal (#20) | Native PAGs | 10292 | 10797 | *19688* | *20492.5* |
| 2 | Monoclonal Trap | Native PAGs | 3444 | *13761* | 5000 | *11024* |
| 3 | Monoclonal Trap | Native PAGs | 3911* | *6947* | *8650* | *9738* |
| 4 | Monoclonal Trap | Native PAGs in NPHS | 7584.5 | 7265 | *16953.5* | *12324.5* |

Table 3, below, shows results from trapping PAGs, using monoclonal antibodies, from sera of two different cows collected from known stages of pregnancy (Days 0, 21, 30, 40, 150 and 200) and detecting the immobilized PAGs via their proteolytic activity. The higher values in samples from D30 onwards are reflective of increasing concentrations of circulating PAG in serum. Numbers in italics are significantly different from the Day 0 control.

TABLE 3

Selectively trapping PAGs from pregnant cow sera as detected by proteolysis of a fluorescently tagged peptidase substrate.

| | Pregnant cow | D0 | D21 | D30 | D40 | D150 | D200 |
|---|---|---|---|---|---|---|---|
| Monoclonal Trap | A | 7214.5 | 4754 | 5584.5 | *8410* | *7653.5* | *9892.5* |
| | B | 3808.5 | 3420 | *8424.5* | 4094 | *8979* | *6370* |

EXAMPLE 5

Immune-Trap Assays of Recombinant PAGs

A commercially available anti-FLAG monoclonal antibody (M2; Sigma, St. Louis, Mo.) was used to selectively immobilize recombinant proteins boPAG-2, boPAG-12 and poPAG-2 by binding to the FLAG peptide present on the amino-terminus of the recombinant proteins (described above). The solution added to the wells was a complex protein mixture consisting of a crude insect cell lysate containing expressed recombinant PAG proteins, or a control insect cell lysate which represented insect cells (sf9 cells) infected with empty Baculovirus. Numbers in italics represent fluorescent product that were significantly greater from the controls. Controls consisted of sf9 lysate, trapping antibody, but no lysate added (Ab-control) and wells containing only buffer and substrate that were used to estimate the background fluorescence. These experiments also included a polyclonal antibody raised against recombinant porcine PAG-2. This antibody was able to specifically trap recombinant poPAG-2, but not boPAG-2 and boPAG-12, from its corresponding lysate. Again, the assayed peptidase activity was significantly higher than the control wells.

TABLE 4

Immuno-trap assay of recombinant PAGs in insect cell lysates.

| | boPAG-2 | boPAG-12 | poPAG-2 | Control lysate | Ab-control | Empty wells |
|---|---|---|---|---|---|---|
| Anti-FLAG | *27048* | *42298* | *96768* | 4116.5 | 3812 | 4008 |
| Anti-FLAG | *26547.5* | *22998.5* | *92254.5* | 7758.5 | 6068.5 | 5299.5 |
| Anti-poPAG-2 | 1783 | 3013 | *10936* | 5717.5 | 4443 | 4469 |

Figure 6A:
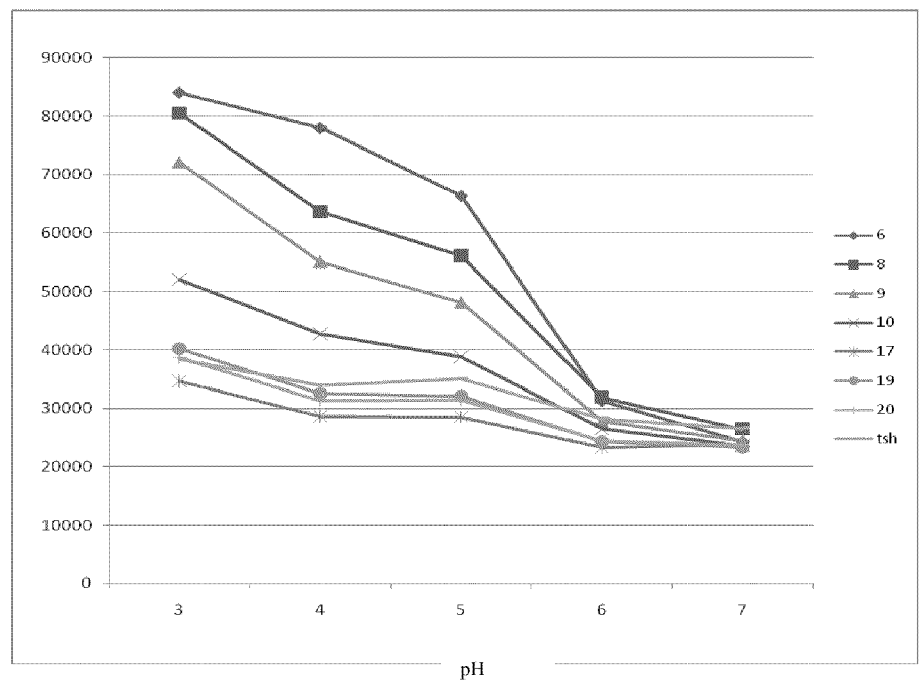
FIGS. 6A and 6B. Relative protease activity, as measured by fluorescence, from an immuno-trap protease assay of several recombinant PAGs isolated with an anti-FLAG monoclonal antibody. The reactions were performed under several pH conditions simultaneously (pH 2.5 to 7.0). Identical concentrations of each recombinant PAG lysate were added to the wells.
Figure 6B:
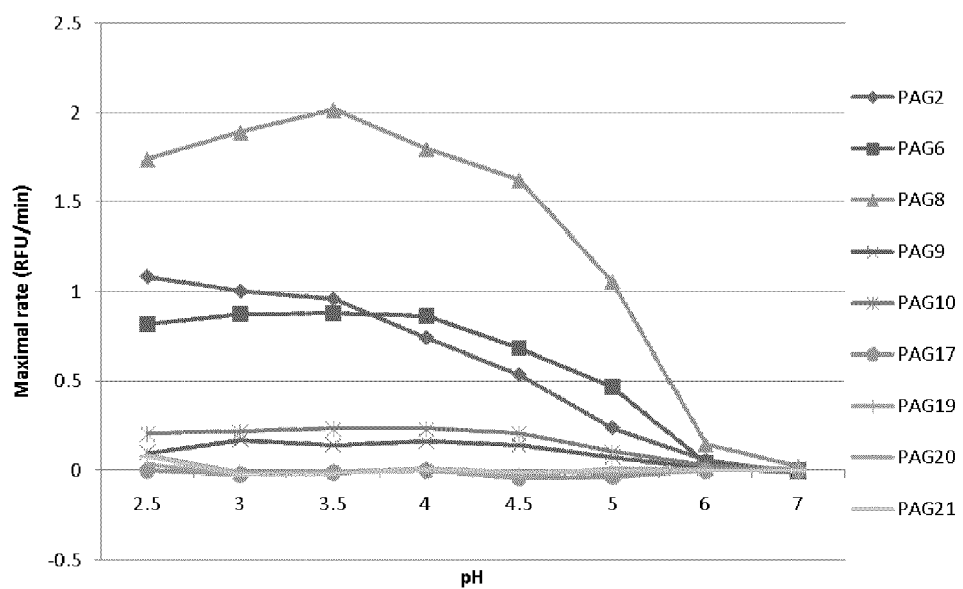

Table 5 and FIGS. 6A and 6B show results of protease activity (fluorescence) from immuno-trap assays of several additional recombinant bovine PAGs that were expressed as fusion proteins with a FLAG epitope tag. The PAGs were immobilized in the wells of an ELISA plate by using anti-FLAG in an immuno-protease assay format (as described above) and were analyzed for their proteolytic activity against the cathepsin D/E FRET substrate at pH increments ranging from 3-7. Recombinant equine-TSH-beta that was expressed and purified in the same manner as the PAGs does not have proteolytic activity. This protein was used as a negative control in the assay to establish the baseline for background fluorescence. Numbers in italics represent readings significantly different from the TSH-beta control protein. The assay shows that recombinant boPAG-6, -8, -9 and -10 have proteolytic activity with acidic pH optima.

TABLE 5

Relative fluorescent product release from recombinant candidate bovine PAGs obtained by using an anti-FLAG immuno-trap protease assay.

| Recombinant PAG | pH 3.0 | pH 4.0 | pH 5.0 | pH 6.0 | pH 7.0 |
| --- | --- | --- | --- | --- | --- |
| 6 | *83970.5* | *77910.5* | *66336.5* | *31300.5* | 24296 |
| 8 | *80567.5* | *63634* | *56086.5* | *31924* | 26426.5 |
| 9 | *72112.5* | *55013* | *48137.5* | 27758 | 24401.5 |
| 10 | *52075* | *42734.5* | *38844* | 26525 | 23581.5 |
| 17 | 34647 | 28612 | 28519.5 | 23267 | 23673 |
| 19 | *40253.5* | *32507.5* | *32086.5* | 24268.5 | 23271.5 |
| 20 | *38630.5* | 31285 | 31407.5 | 24524.5 | 23780 |
| tsh (control) | 38349 | 33908 | 34996.5 | 28222.5 | 26590.5 |

Table 6 shows results from an assay demonstrating how candidate PAGs can be differentially recognized by anti-PAG monoclonal antibodies. Numbers in italics represent readings significantly different from controls. The results indicate that bovine PAGs 6, 8 and 9 were identified by each of the individual monoclonals (A6, L4, J2) as well as a mixture of them ("Mixed"). The monoclonal antibodies were described in some detail elsewhere (Green et al., 2005). PAG-10 was not trapped by any of the candidate monoclonals, which was not unexpected since PAG-10 is quite distinct from the other PAGs being tested. The monoclonals either have no affinity for PAG-21 or it is proteolytically inactive under the tested conditions. TSH-beta was used as a negative control to establish the background level of fluorescence. For comparison, an anti-flag antibody (FLAG) control and poPAG-2 lysate were used as a positive controls for the experiment.

TABLE 6

Relative fluorescent product release from recombinant candidate bovine PAGs obtained by using an immuno-trap protease assay with PAG-specific monoclonal antibodies.

| Monoclonal | 6 | 8 | 9 | 10 | 21 | TSH-beta |
| --- | --- | --- | --- | --- | --- | --- |
| Mixed | *64554* | *85319.5* | *89343* | 48468.5 | 53946 | 53027 |
| A6 | *67510* | *81389.5* | *91777.5* | 52183.5 | 55432.5 | 52778 |
| L4 | *66321.5* | *80958* | *91452.5* | 54533 | 57730 | 53980.5 |
| J2 | *62766.5* | *86421.5* | *97480.5* | 57481 | — | — |
| | poPAG-2 | tsh-beta | | | | |
| FLAG | *97357* | 47019.5 | | | | |

EXAMPLE 6

Use of Synthetic Fluorescent Substrate Libraries to Determine PAG Specificities

The studies described in Examples 1-5 were performed using a commercially available cathepsin D/E substrate (e.g. Peptides International, cat. No. SMO-3200-v). Specificity in those assays was achieved by using PAG-specific antibodies. However, specificity could also be achieved by identifying substrates that are preferentially cleaved by PAGs in general (and not by other proteinases) or by distinct PAGs (but not all of them). Such substrates could provide even greater target specificity when used in an immune-trap protease assay, and can also be employed by themselves as substrates, to be added to a heterogeneous protein sample (e.g. plasma, serum, milk). The presence of a PAG or PAGs in the sample could then be determined by the amount of product formation that ensues.

Figure 8A:
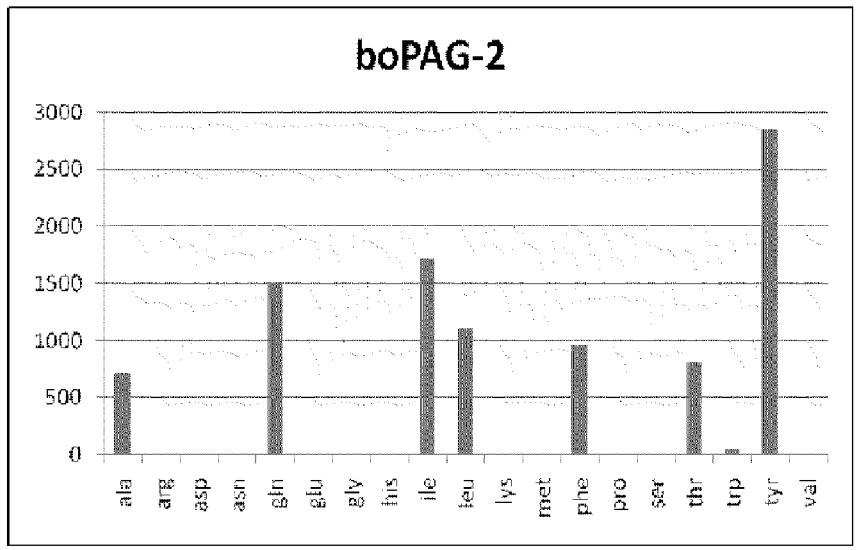
FIGS. 8A and 8B. Relative fluorescence release upon incubation of peptide library with boPAG-2 (FIG. 8A); or boPAG-12 (FIG. 8B). Initial velocities were obtained from the proteolysis of the respective substrate libraries designated by the three letter amino acid code. The libraries are named after the amino acid occupying position-X in the library. The velocities obtained from boPAG-2 and -12, against each representative substrate library, are showed in panels A (boPAG2) and B (boPAG-12).
Figure 8B:
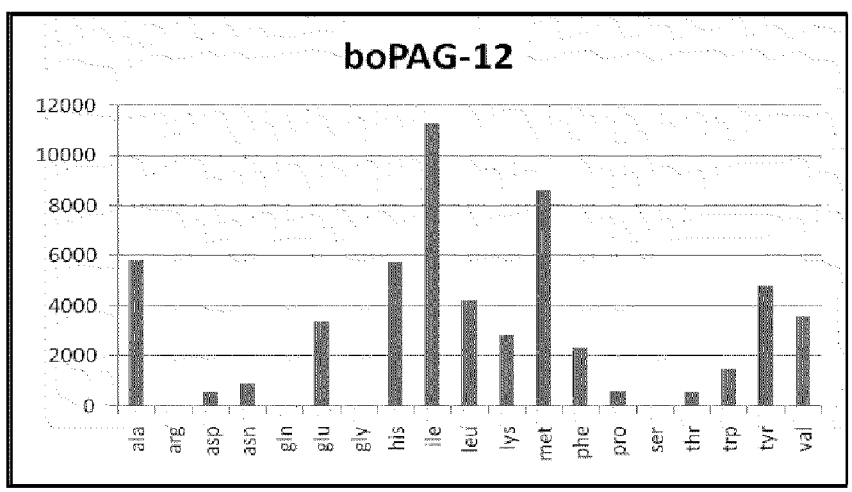

Thus, a combinatorial FRET-25× peptide library (FIG. 7) with a fluorescent label was tested as substrate with two related members of the PAG family (boPAG-2 and boPAG-12), to determine if a cleavable substrate for boPAG-2 or boPAG-12 happened to be present in the mixture. As shown in FIG. 7, NMA is the fluorescent donor and DNP is the fluorescence quencher. The right most degenerate position in FIG. 7, "Xaa," represents one of 19 natural amino acids with the exception of cysteine. There are 5 amino acid residues potentially present at the position "Yaa", and 5 at position "Zaa". The sub-libraries are named based on the specific residue present in the Xaa position as shown in FIG. 7. These libraries are available commercially; the ones employed in these experiments were from Peptides International (sequential catalog numbers: SFA-3701-v to SFA-3719-v). Sub-libraries were used as substrates, and relative fluorescence was measured to determine if a cleavable substrate was present. The results of the assay are shown in FIGS. 8A and 8B. The different rates of proteolysis, and, by extension, the relative affinity for the substrates present in each library, by boPAG-2 and boPAG-12 demonstrated that there are differences in their respective substrate specificities, which supports the premise that it would be possible to identify PAG-specific substrates that may be used for specific detection of a certain PAG.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference:
U.S. Pat. No. 3,646,346; U.S. Pat. No. 3,817,837; U.S. Pat. No. 3,850,752; U.S. Pat. No. 3,939,350; U.S. Pat. No.

3,996,345; U.S. Pat. No. 4,275,149; U.S. Pat. No. 4,277,437; U.S. Pat. No. 4,366,241; U.S. Pat. No. 4,367,110; U.S. Pat. No. 4,376,110; U.S. Pat. No. 4,452,901; U.S. Pat. No. 4,668,621; U.S. Pat. No. 4,699,880; U.S. Pat. No. 5,721,105; U.S. Pat. No. 6,869,770

U.S. Patent Publn. 2003/508381; U.S. Patent Publn. 2003/0073248; U.S. Patent Pubn. 20050100975; U.S. Patent Publn. 2007/0184558

Abbondanzo et al., *Breast Cancer Res. Treat.*, 16:182(151), 1990.

Allred et al., *Breast Cancer Res. Treat.*, 16:182(149), 1990.

Atkinson et al., *J. Biol. Chem.*, 268(35):26679-26685, 1993.

Ausubel et al., In: *Current Protocols in Molecular Biology*, John, Wiley & Sons, Inc, N.Y., 1994; 1992.

Beal et al., *J. Anim. Sci.*, 70:924-929, 1992.

Beyer et al. *Biochemistry* 44:1768-1779, 2005.

Biocomputing: Informatics and Genome Projects, Smith (Ed.), Academic Press, NY, 1993.

Bischof, *Am. J. Perinatol.* 6:110-116, 1989.

Bischoff *Early Pregnancy* 5:30-31, 2001.

Boulianne et al., *Nature*, 312:643-646, 1984.

Brown et al., *Breast Cancer Res. Treat.*, 16: 192 (#191), 1990.

Butler et al., *Biol. Reprod.*, 26:925-933, 1982.

Cabilly et al., *Proc. Natl. Acad. Sci. USA*, 91:3273-3277, 1984.

Cameron and Malmo, *Austr. Vet. J.*, 70:109-111, 1993.

Capaldi et al., *Biochem. Biophys. Res. Comm.*, 76:425, 1977.

Chardes et al., *FEBS Lett.*, 452(3):386-394, 1999.

Clements et al. *Crit. Rev. Clin. Lab. Sci.* 41:265-312, 2004.

Colligan et al., In: *Current Protocols in Immunology*, Greene Publ. Assoc. Wiley Interscience, NY, 1993.

Computational Molecular Biology, Lesk (Ed.), Oxford University Press, NY, 1988.

Computer Analysis of Sequence Data, Part I, Griffin and Griffin (Eds.), Humana Press, NJ, 1994.

Cumber et al., *J. Immunology*, 149B:120-126, 1992.

Davies *Ann. Rev. Biophys. Biophys. Chem.* 19:189-215, 1990.

Deegan et al., *Blood Cell Mol. Dis.* 35:259-267, 2005.

Dunn *Chem. Rev.* 102:4431-4458, 2002.

Engvall, *Lancet*, 2(8000):1410, 1976.

Engvall, *Med. Biol.*, 55(4):193-200, 1977.

Engvall, *Methods Enzymol.*, 70(A):419-39, 1980.

Green et al., *Theriogenology*, 63(5):1481-1503, 2005.

Green et al., *Biol. Reprod.* 62:1624-1631, 2000.

Green et al., *Biol. Reprod.* 60:1069-1077, 1999.

Green, et al., *Theriogenology* 63:1481-1503, 2005.

Gripenberg et al., *Scand. J. Immunol.*, 7(2):151-7, 1978.

Guruprasad et al., *Protein Engin.*, 9:849-856, 1996.

Harlow and Lane, In: *Antibodies, a Laboratory Manual*, Cold Spring Harbor Laboratory, pp 139-281, 1988.

Hatzidakis et al., *J. Reprod. Fertil.*, 98:235-240, 1993.

Higgins and Sharp CABIOS. 5:151-153 (1989

Holdsworth et al., *J. Endocrin.*, 95:7-12, 1982.

Hughes et al., *Mol. Biol. Evol.* 20:1940-1945, 2003.

Hughes *Proc. Nat. Acad. Sci. USA* 97:3319-3323, 2000.

Irwin et al., *Endocrinol.* 141:666-674, 2000.

Klisch & Leiser, *Histochem Cell Biol.*, 119:211-217, 2003.

Klisch et al., *Reproduction* 132:791-798, 2006.

Kohler and Milstein, *Nature*, 256:495-497, 1975.

Leibiger et al., *Biochem. J.*, 338:529-538, 1999.

Liu et al. *Cell Mol. Biol.*, 49(2):209-216, 2003.

Makler et al., *Transfusion*, 21(3):303-312, 1981.

Markusfeld et al., *Br. Vet. J.*, 146: 504-508, 1990.

Mo et al., *Eur. J. Immunol.*, 23:2503-2510, 1993.

Murooka and Yamashita, *J. Biosci. Bioeng.* 91:433-441, 2001.

Nakamura et al., In: *Handbook of Experimental Immunology* ($4^{th}$ Ed.), Weir et al. (Eds.), 1:27, Blackwell Scientific Publ., Oxford, 1987.

Neuberger et al., *Nature*, 314:268-270, 1985.

Nomura et al., *Biochem. Biophys. Acta* 1751:19-25, 2005.

Oltenacu et al., *J. Dairy Sci.*, 73:2826-2831, 1990.

O'Reilly, et al. *Baculovirus expression vectors*: A laboratory manual. W.H. Freeman and Company, 1992.

Pack et al., *Biochem.*, 31:1579-1584, 1992.

Poisner, *Neuroendocrinol.* 19:232-252, 1998.

PCT Appln. WO 98/16832

Sarngadharan et al., *Princess Takamatsu Symp.*, 15:301-8, 1984.

Sequence Analysis in Molecular Biology, von Heinje (Ed.), Academic Press, 1987.

Sequence Analysis Primer, Gribskov and Devereux (Eds.), Stockton Press, NY, 1991.

Sidikou et al., *Res. Vet. Sci.* 80:260-266, 2005,

Szafranska et al., *Biol. Reprod.*, 53:21-28, 1995.

Telugu et al., pp. 41-43 in *Maternal Recognition of Pregnancy in the mare III.*, Strout TAE and Wade J F, Eds. Havemeyer Foundation Monograph, Series No. 16. R and W communications, UK. Proceedings held 13-16 Nov. 2004.

Twinging, *Anal. Biochem.* 143:30-34, 1984.

Villanueva et al. *J. Clin. Invest.* 116:271-284, 2006

Wagner et al., *Science*, 260(5113):1510-1513, 1993

Warnick et al., *Theriogenol.*, 44:811-825, 1995.

Wooding, et al., *Placenta* 26:807-827, 2005.

Wu et al., *Clin. Chem.* 50:125-129, 2004.

Xie et al., *Biol. Reprod.*, 51:1145-1153, 1994.

Xie et al., *Biol. Reprod.*, 54: 122-129, 1996.

Xie et al., *Biol. Reprod.*, 57:1384-1393, 1997.

Xie et al., *Proc. Natl. Acad. Sci. USA*, 88:10247-10251, 1991.

Xie et al., *Proc Natl Acad Sci* 94:12809-12816, 1997.

Zitouni et al., *Diabetes Care* 28:1698-1703, 2005.

Zoli et al., *Biol. Reprod.*, 45:1-10, 1991.

What is claimed is:

1. A method for the detection of pregnancy in an Artiodactyl animal comprising:
   (a) obtaining a sample comprising at least one pregnancy-associated glycoprotein (PAG) with proteolytic activity from the animal;
   (b) contacting the sample with a substrate for proteolysis; and
   (c) detecting proteolytic activity of said PAG in the sample, wherein an elevated level of proteolytic activity relative to the level in a non-pregnant Artiodactyl animal indicates that the animal is pregnant.

2. The method of claim 1, wherein the Artiodactyl animal is a bovine animal.

3. The method of claim 1, wherein the sample is obtained from the animal at days 16 to 30 post-insemination.

4. The method of claim 3, wherein the sample is obtained from the animal at day 20, 21, 22, 23, 24, 25, 26, 27 or 28 post-insemination.

5. The method of claim 1, wherein detecting comprises measuring the level of proteolytic activity of more than one PAG.

6. The method of claim 1, wherein the PAG is selected from the group consisting of boPAG-2, boPAG-6, boPAG-8, boPAG-9, boPAG-10, boPAG-12, and poPAG-2.

7. The method of claim 1, comprising detecting said PAG in early pregnancy.

8. The method of claim 1, wherein the sample is selected from the group consisting of serum, plasma, whole blood, milk or urine.

9. The method of claim 1, comprising detecting said PAG at day 50 to day 250 of pregnancy.

10. The method of claim 1, wherein the PAG is present in early pregnancy and absent at about two months post-partum.

11. The method of claim 1, wherein the proteolytic activity is inhibited by pepstatin A.

12. The method of claim 1, wherein detecting proteolytic activity in the sample comprises detection of a product of proteolysis.

13. The method of claim 12, wherein detection comprises a colorimetric, luminescent, or fluorescent method.

14. The method of claim 1, wherein the substrate for proteolysis is selected from the group consisting of a cathepsin D substrate, a cathepsin E substrate, and a peptide comprising SEQ ID NO:2.

15. The method of claim 1, wherein proteolytic activity is measured at a pH of about 2.5 to about 7.0.

16. The method of claim 15, wherein proteolytic activity is measured at a pH of between about 2.5 and about 5.5.

17. The method of claim 15, wherein proteolytic activity is measured at a pH of between about 3 and about 5.

18. The method of claim 1, further comprising increasing the proportion of PAG in the sample prior to step (b) or step (c).

19. The method of claim 18, wherein increasing the proportion of PAG in the sample comprises contacting the sample with a lectin or with an antibody.

20. The method of claim 19, wherein increasing the proportion of PAG comprises contacting PAG with a monoclonal or polyclonal antibody that specifically binds to PAG.

21. The method of claim 20, wherein the polyclonal or monoclonal antibody is selected from the group consisting of 2D9, A6, L4, and J2.

22. The method of claim 1, wherein at least about 1 ng of a proteolytically active boPAG is present per sample.

23. The method of claim 22, wherein at least about 5 ng of a proteolytically active boPAG is present per sample.

24. The method of claim 22, wherein at least about 10 ng of a proteolytically active boPAG is present per sample.

* * * * *